US007135182B2

(12) United States Patent
Sundstrom et al.

(10) Patent No.: US 7,135,182 B2
(45) Date of Patent: Nov. 14, 2006

(54) INHIBITION OF TRANSGLUTAMINASE-MEDIATED MICROBIAL INTERACTION WITH A MAMMALIAN HOST

(75) Inventors: Paula Sundstrom, Columbus, OH (US); Steven D. Bradway, Aberdeen, WA (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 10/117,121

(22) Filed: Apr. 8, 2002

(65) Prior Publication Data

US 2002/0122804 A1 Sep. 5, 2002

Related U.S. Application Data

(62) Division of application No. 09/178,509, filed on Oct. 26, 1998, now Pat. No. 6,388,056.

(51) Int. Cl.
*C07K 14/40* (2006.01)

(52) U.S. Cl. ............... 424/185.1; 424/184.1; 424/130.1; 424/139.1; 424/141.1; 424/142.1; 424/152.1; 424/172.1; 530/350; 530/387.1; 530/387.9; 530/388.1; 530/388.15; 530/389.1

(58) Field of Classification Search ............ 424/184.1, 424/185.1, 130.1, 139.1, 141.1, 142.1, 152.1, 424/172.1; 530/350, 387.1, 387.9, 388.1, 530/388.15, 389.1
See application file for complete search history.

(56) References Cited

OTHER PUBLICATIONS

Sundstrom et al. (Journal of Infectious Diseases, vol. 185, pp. 521-530, 2002).*
Bowie et al (Science, 1990, 257:1306-1310).*
Dermer (Bio/Technology, 1994, vol. 12 p. 320).*
Freshney (Culture of Animal Cells, A Manual of Basic Technique, Alan R. Liss, Inc., 1983, New York, p. 4).*
J. Staab et al., *J. Biol. Chem.*, 271(11) 6298-6305 (Mar. 1996).
J. Staab et al., *Yeast*, 14, 681-686 (1998).
J. Staab et al., *Database EMBL* (online), Accession No. U64206 (Apr. 1997).
J. Staab et al., *Abstracts of the General Meeting of the American Society for Microbiology*, 97(0), 339 (May 1997).
X. Wang et al., *Abstracts of the General Meeting of the American Society for Microbiology*, 97(0), 596 (May 1997),
J. Staab et al., *Science*, 283, 1535-1538 (Mar. 5, 1999).
P. Sundstrom, *Curr. Opin. Microbiol.*, 2(4), 353-357 (Aug. 1999).
L. Sharkey et al., *Database EMBL* (online), Accession No. AF001978 (Jun. 1997).
L. Sharkey et al., *J. Bact.*, 181(17), 5273-5279 (Sep. 1999).
P. Sundstrom et al., *Infection and Immunity*, 55(3), 616-620 (Mar. 1987).
AAB64014 Genbank Jun. 23, 1997.

* cited by examiner

*Primary Examiner*—Robert A. Zeman
(74) *Attorney, Agent, or Firm*—Licata & Tyrrell P.C.

(57) ABSTRACT

The infection of a mammalian host by a microorganism can be prevented or treated through the administration of substrates for transglutaminases or antibodies against such substrates that inhibit the transglutaminase-mediated interaction of the microorganism with the mammalian host. These compounds may be used in the identification, prevention or treatment of microbial infection of mammalian hosts such as immunocompromised or immunosuppressed humans, for example, those having AIDS or undergoing transplantation or anti-cancer therapy.

1 Claim, 9 Drawing Sheets

Ser Tyr Asp Tyr Tyr Gln Glu Pro Cys
40            45
Asp Asp Tyr Pro Gln Gln Gln Gln Gln Gln Glu Pro Cys Asp Tyr Pro
50            55            60
Gln Gln Gln Gln Gln Glu Glu Pro Cys Asp Tyr Pro Gln Gln Gln Pro
65            70            75            80
Gln Glu Pro Cys Asp Tyr Pro Gln Gln Pro Gln Glu Pro Cys Asp Tyr
85            90            95
Pro Gln Gln Pro Gln Glu Pro Cys Asp Tyr Pro Gln Gln Pro Gln Glu
100            105            110
Pro Cys Asp Asn Pro Pro Gln Pro Asp Val Pro Cys Asp Asn Pro Pro
115            120            125
Gln Pro Asp Val Pro Cys Asp Asn Pro Pro Gln Pro Asp Ile Pro Cys
130            135            140
Asp Asn Pro Pro Gln Pro Asp Ile Pro Cys Asp Asn Pro Pro Gln Pro
145            150            155            160
Asp Gln Pro Asp Asp Asn Pro Pro Ile Pro Asn Ile Pro Thr Asp Trp
165            170            175
Ile Pro Asn Ile Pro Thr Asp Trp Ile Pro Asp
180            185

FIG. 1

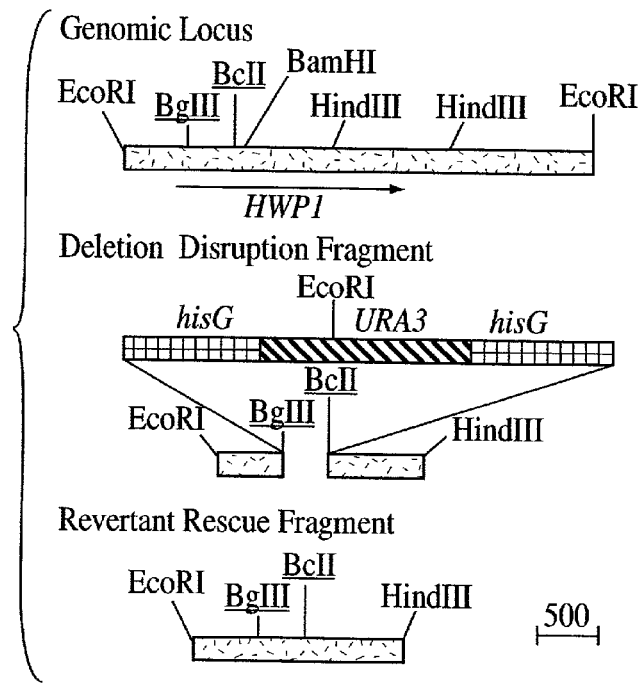
FIG. 3A
FIG. 3B
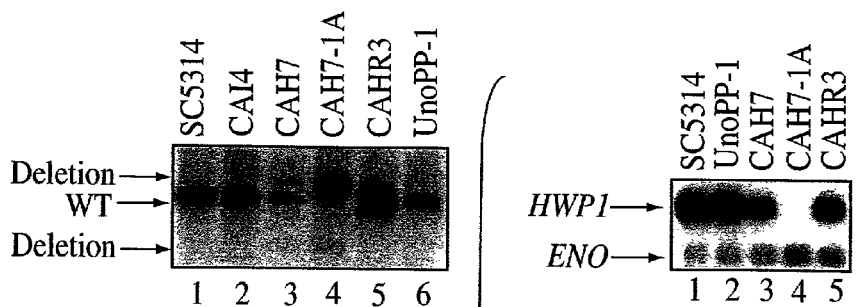
Ratio of *HWP1* and enolase mRNA's
| Strain | HWP1/ENO* |
|---|---|
| SC5314 (wt) | 13.09 |
| UnoPP-1 (*HWP1/HWP1*) | 14.39 |
| CAH7 (*hwp1/HWP1*) | 5.96 |
| CAH7-1A (*hwp1/hwp1*) | 0.00 |
| CAHR3 (*HWP1/hwp1*) | 5.36 |
*Average ratio determined from two experiments
FIG. 3C

```
                       t cttatgatta  ctatcaagaa  ccatgtgatg  attacccaca
 661 acaacaacaa caacaagagc cttgtgatta  cccacaacaa  caacagcagg  aagaaccttg
 721 tgattaccca  caacaacaac cacaagagcc atgtgactat  ccacaacagc cacaagaacc
 781 ttgtgactac  ccacaacaac cacaagaacc ttgtgactac  ccacaacaac cacaagaacc
 841 ttgcgacaat  ccacctcaac ctgatgttcc ttgtgacaat  cctcctcaac ctgatgttcc
 901 ttgtgacaat  cctcctcaac ctgatattcc ttgtgacaat  cctcctcaac ctgatattcc
 961 ttgtgacaat  cctcctcaac ctgatcagcc tgatgacaat  cctcctattc  caaacattcc
1021 aaccgattgg  attccaaata  ttccaactga ttggatccca  gat
```

FIG. 7

```
                         SEQUENCE LISTING

<160> NUMBER OF SEQ ID NOS: 2

<210> SEQ ID NO 1
<211> LENGTH: 148
<212> TYPE: PRT
<213> ORGANISM: Candida albicans

<400> SEQUENCE: 1

Ser Tyr Asp Tyr Tyr Gln Glu Pro Cys Asp Asp Tyr Pro Gln Gln Gln
  1               5                  10                  15

Gln Gln Gln Glu Pro Cys Asp Tyr Pro Gln Gln Gln Gln Gln Glu Glu
             20                  25                  30

Pro Cys Asp Tyr Pro Gln Gln Gln Pro Gln Glu Pro Cys Asp Tyr Pro
         35                  40                  45

Gln Gln Pro Gln Glu Pro Cys Asp Tyr Pro Gln Gln Pro Gln Glu Pro
     50                  55                  60

Cys Asp Tyr Pro Gln Gln Pro Gln Glu Pro Cys Asp Asn Pro Pro Gln
 65                  70                  75                  80

Pro Asp Val Pro Cys Asp Asn Pro Pro Gln Pro Asp Val Pro Cys Asp
                 85                  90                  95

Asn Pro Pro Gln Pro Asp Ile Pro Cys Asp Asn Pro Pro Gln Pro Asp
            100                 105                 110

Ile Pro Cys Asp Asn Pro Pro Gln Pro Asp Gln Pro Asp Asp Asn Pro
        115                 120                 125

Pro Ile Pro Asn Ile Pro Thr Asp Trp Ile Pro Asn Ile Pro Thr Asp
    130                 135                 140

Trp Ile Pro Asp
145

<210> SEQ ID NO 2
<211> LENGTH: 444
<212> TYPE: DNA
<213> ORGANISM: Candida albicans
```

```
<400> SEQUENCE: 2
tcttatgatt actatcaaga accatgtgat gattacccac aacaacaaca acaacaagag        60
ccttgtgatt acccacaaca acaacagcag gaagaacctt gtgattaccc acaacaacaa       120
ccacaagagc catgtgacta tccacaacag ccacaagaac cttgtgacta cccacaacaa       180
ccacaagaac cttgtgacta cccacaacaa ccacaagaac cttgcgacaa tccacctcaa       240
cctgatgttc cttgtgacaa tcctcctcaa cctgatgttc cttgtgacaa tcctcctcaa       300
cctgatattc cttgtgacaa tcctcctcaa cctgatattc cttgtgacaa tcctcctcaa       360
cctgatcagc ctgatgacaa tcctcctatt ccaaacattc caaccgattg gattccaaat       420
attccaactg attggatccc agat                                              444
```

INHIBITION OF TRANSGLUTAMINASE-MEDIATED MICROBIAL INTERACTION WITH A MAMMALIAN HOST

CROSS REFERENCE TO RELATED APPLICATION

The present application is a divisional of and claims, under 35 U.S.C. § 120, the benefit of U.S. patent application Ser. No. 09/178,509, filed on 26 Oct. 1998, now U.S. Pat. No. 6,388,056, issued on 14 May 2002, which is expressly incorporated fully herein by reference.

STATEMENT REGARDING FEDERALLY SPONSORED RESEARCH

This invention was made, at least in part, with US government support under grant number 2R01DE011375, awarded by NIH. The US government may have certain rights in the invention.

FIELD OF THE INVENTION

The present invention relates to compounds and methods for the prevention and treatment of microbial infection of a mammalian host through the administration of substrates for transglutaminases or antibodies against such substrates that inhibit the transglutaminase-mediated interaction of the microorganism with the mammalian host. These compounds and methods may be used preferably in the identification, prevention or treatment of microbial infection of mammalian hosts such as immunocompromised or immunosuppressed humans, for example, those having AIDS or undergoing transplantation or anti-cancer therapy.

BACKGROUND OF THE INVENTION

Whether pathogenic or opportunistic, microorganisms have evolved numerous mechanisms to facilitate their establishment and proliferation in mammalian hosts. During initial infection, the interaction of a microorganism with its mammalian host can include attachment or adhesion to the host cell surface, invasion of host cells, and elaboration of toxins, for example. In certain instances, this interaction can be nonspecific. In others, such microbial interaction involves the specific binding of the microorganism to a particular receptor or receptor complex expressed on the host cell surface. In turn, the binding event can trigger changes in the microorganism and/or the mammalian host cell, leading to the progression of infection.

The host cell functions of molecules involved in certain microbial interaction are unknown in some cases and known in others. Mammalian transglutaminases are examples of those in the latter category for which the molecular mechanism of action and/or role in host cell growth or development has been elucidated. In general, transglutaminases are enzymes that catalyze intermolecular crosslinks by the formation of highly stable isodipeptide bonds between the γ-carbonyl group of glutamine and the ε-amino group of lysine residues, which are resistant to proteases, sodium dodecyl sulfate and heat. Epithelial cell transglutaminases are important for the formation of cornified envelopes of mature squamous epithelial cells.

Only recently have investigators shown that certain microorganisms may express proteins capable of acting as substrates for, and thus interact with, mammalian transglutaminases. One example is hyphal wall protein 1 (Hwp1), which is expressed on hyphal surfaces of the pathogenic fungus, Candida albicans. Hwp1 consists of an N-terminal proline and glutamine-rich repetitive amino acid sequence that is exposed on the hyphal surface, and a cell wall-anchored serine and threonine-rich C-terminus. The composition of the N-terminal amino acid repeats is reminiscent of mammalian transglutaminase substrates. It is now known that Hwp1 can serve as a substrate in transglutaminase-mediated cross-linking reactions.

Candida is an ubiquitous yeast recognized as the causative agent of candidiasis (Candida mycosis). At least 90% of the disorders are caused by the species C. albicans, which is an opportunistic yeast able only to elicit mild superficial infections in normal individuals. Fungal infections associated with severe infections of the mucous membrane and with invasive infections of individual organs are observed ever more frequently as a result of the increasing number of patients with immune defense weakness, e.g., patients with acquired immunodeficiency syndrome (AIDS) or patients undergoing immunosuppressive therapy.

If left untreated, such systemic infections frequently lead to the death of the patients. At present, the treatment for invasive infections is based on relatively few antimycotics, such as amphotericin B and flucytosine, or the azole derivatives fluconazole and itraconazole. These antimycotics cause serious, sometimes different, side effects, such as renal insufficiency, hypocalcemia and anemia, as well as unpleasant constitutional symptoms such as fever, shivering and low blood pressure.

For this reason, doctors and clinicians are interested, for achieving direct and effective therapy, in having available diagnostic procedures permitting the earliest possible identification of the fungal pathogens. Conventional methods of diagnosis are based on the in vitro cultivation of the pathogens and the identification of the fungal species by means of morphological, physiological and biochemical methods. The culturing of C. albicans from blood is frequently very difficult and unreliable. Although C. albicans can be cultured from the mouths of normal persons, the progression to mucosal candidiasis is characterized by a shift in the microbial flora that includes an increase in the number of fungi in saliva, followed ultimately by invasion and inflammation of the gastrointestinal mucosa by C. albicans. The clinical presentations are pseudomembranous or erythematous lesions in the oral cavity and/or esophagus.

Oropharyngeal and esophageal candidiasis are among the most frequent opportunistic fungal infections observed in human immunodeficiency virus positive (HIV+) and AIDS patients, occurring in the majority of patients. The pathogenesis is complex and is thought to involve multiple host factors that include loss of cell mediated immunity and altered phagocytic cell activity. The current status of the AIDS epidemic is one of increasing numbers of individuals infected and no cure. Many infected individuals may live for a long time with HIV in an essentially permanent immunocompromised state. Because of the loss of the cellular component of the immune system, AIDS patients are susceptible to invasion of submucosal tissue by C albicans. The frequency of candidal infections may also be a result of the prophylactic use of antibacterial drugs used in AIDS patients to minimize other opportunistic infections. Candidal infections increase in severity and recur more frequently as the immunodeficiency progresses.

While treatment with antifungal drugs can be effective, the increasing frequency of resistant strains of C. albicans, and the systemic side effects of the drugs exploration of novel strategies to interrupt the sequence of events leading to disease and to expand the repertoire of antifungal drugs. An antifungal strategy based on biological interactions between C. albicans and the oral mucosa would be of great benefit to those with such fungal infections, e.g., patients with long-term immunodeficiencies.

Relevant features of C. albicans, the most frequent cause of oral candidiasis in HIV infected patients, are persistence in the gastrointestinal mucosa and invasiveness in the presence of diminished host defenses. Although C. albicans is sensitive to antifungal drugs, treatment over long periods of time are required, and isolates from HIV infected patients may be more resistant than other isolates. In addition to HIV infected patients, oral candidiasis occurs in patients with leukemia or other cancers, as well as in patients with other underlying diseases. Candidiasis in denture wearers, or denture stomatities, is the commonest of all C. albicans associated diseases. Indeed, new approaches towards preventing or managing oral candidiasis are needed.

A feature of C. albicans growth that is correlated with pathogenicity in the oral cavity is the ability to transform from budding to filament-extending growth. Filamentous forms adhere more readily to buccal epithelial cells than budding yeasts, and histologically are a prominent feature of invasion of the mucosa. Knowledge of the molecular events that transform C. albicans to the pathogenic filamentous form as well as detailed investigations of the hyphal surface at the molecular level are necessary for understanding the pathogenesis of oral candidiasis.

In mucosal and systemic disease, C. albicans exists as a polymorphic set of growth forms termed yeasts, pseudohyphae and true hyphae. In mucosal disease, filamentous forms, particularly true hyphae, invade the keratinized layer of differentiated, stratified squamous epithelium. True hyphae are septate, cylindrical structures with parallel sides that are formed by extension of germ tubes which emerge from yeasts in appropriate environmental conditions.

In the oral mucosa, Hwp1 adherence may help C. albicans resist the mechanical forces that clear the oral mucosa, enhancing colonization. Hwp1-mediated stabilized adhesion may induce accelerated maturation of epithelial cells, partially explaining the association of candidiasis with increased turnover of basal keratinocytes. Alternatively, Hwp1 may be important for interacting with host transglutaminases other than those associated with epithelial cells. Hwp1 may also be important for the spatial expression of other pathogenically-important proteins on the germ tube surface.

A valuable contribution to the art therefore would be compounds and methods for the prevention and treatment of microbial infection of a mammalian host through the administration of substrates for transglutaminases or antibodies against such substrates that inhibit the transglutaminase-mediated interaction of the microorganism with the mammalian host. These compounds and methods may be used preferably in the identification, prevention or treatment of microbial infection of mammalian hosts such as inmmunocompromised humans having AIDS.

SUMMARY OF THE INVENTION

Accordingly, an objective of the present invention includes compounds and methods for the prevention and treatment of a microbial infection of a mammalian host through the administration of substrates for transglutaminases or antibodies against such substrates that inhibit the transglutaminase-mediated interaction of the microorganism with the mammalian host.

Another objective pertains to compounds and methods for the identification, prevention or treatment of microbial infection of mammalian hosts such as immunocompromised humans having AIDS. Yet another objective relates to the identification of the absence or presence of microbial infection and the site(s) of such infection. A further objective is a diagnostic kit for such identification. One other objective of the present invention is the prevention and treatment of a microbial infection of a mammalian host through gene therapy, whereby host cells, for example, are engineered to express substrates for transglutaminases that inhibit the transglutaminase-mediated interaction of the microorganism with the mammalian host. These and other objectives are achieved through the following preferred embodiments.

One aspect of the invention is a purified polypeptide comprising the amino acid sequence of SEQ. ID NO. 1, wherein said polypeptide is capable of acting as a substrate for mammalian transglutaminases. Another aspect is an isolated DNA molecule encoding the polypeptide having the amino acid sequence of SEQ. ID NO. 1, and an isolated DNA molecule comprising the nuciotide sequence encoding the polypeptide of SEQ. ID NO. 1. A further aspect is a nucleic acid capable of hybridizing under high stringency conditions to the DNA molecule of an isolated DNA molecule comprising the nucleotide sequence encoding the polypeptide of SEQ. ID NO. 1. In addition, an aspect of the invention is a vector comprising DNA encoding the polypeptide of SEQ. ID NO. 1, a host cell transformed with that vector, and that transformed host cell which produces a protein capable of acting as a substrate for mammalian transglutaminases.

An aspect of the present invention is an isolated antibody against the polypeptide comprising the amino acid sequence of SEQ. ID NO. 1 (or an antigenic portion thereof), wherein said polypeptide (or an antigenic portion thereof) is capable of acting as a substrate for mammalian transglutaminases. In a preferred embodiment, the antibody is a monoclonal antibody. In another preferred embodiment, the antibody is capable of inhibiting the interaction of a microorganism with a mammalian cell, preferably where the microorganism is a bacteria or yeast, and more preferably where the microorganism is C. albicans. In one other preferred embodiment of the antibody, the mammalian cell is a human cell, preferably an epithelial cell, more preferably a mucosal epithelial cell, and most preferably a buccal epithelial cell.

Another aspect of the invention is a method of preventing or treating infection by a microorganism of a mammalian host comprising the steps of administering to said host an effective amount of purified Hwp1 protein, antibody against said Hwp1 protein, or polypeptide comprising the amino acid sequence of SEQ. ID NO. 1, wherein said polypeptide is capable of acting as a substrate for mammalian transglutaminases, antibody against said polypeptide, purified proline-rich protein, or antibody against said proline-rich protein, in a pharmaceutically acceptable sterile vehicle, and inhibiting the interaction of said microorganism with the cells of said host. In another preferred embodiment, the antibody is capable of inhibiting the interaction of a microorganism with a mammalian cell, preferably where the microorganism is a bacteria or yeast, and more preferably where the microorganism is C. albicans. In one other preferred embodiment, the mammalian cell is a human cell, preferably an epithelial cell, more preferably a mucosal epithelial cell, and most preferably a buccal epithelial cell.

In yet another preferred embodiment, the administering is performed orally. In a preferred embodiment, the mammalian host is immunocompromised, and in another, the infection is associated with AIDS.

Another aspect of the invention is a vaccine for preventing infection by a microorganism of a mammalian host comprising an effective amount of purified Hwp1 protein, antibody against said Hwp1 protein, or polypeptide comprising the amino acid sequence of SEQ. ID NO. 1, wherein said polypeptide is capable of acting as a substrate for mammalian transglutaminases, antibody against said polypeptide, purified proline-rich protein, or antibody against said proline-rich protein, in a pharmaceutically acceptable sterile vehicle, wherein said vaccine is capable of inhibiting the interaction of said microorganism with the cells of said host. In another preferred embodiment, the vaccine is capable of inhibiting the interaction of a microorganism with a mammalian cell, preferably where the microorganism is a bacteria or yeast, and more preferably where the microorganism is *C. albicans*. In one other preferred embodiment, the mammalian cell is a human cell, preferably an epithelial cell, more preferably a mucosal epithelial cell, and most preferably a buccal epithelial cell. In yet another preferred embodiment, the administering is performed orally. In a preferred embodiment, the mammalian host is immunocompromised, and in another, the infection is associated with AIDS.

An aspect of the present invention is a diagnostic kit for detecting the presence or absence of a microorganism expressing a protein capable of acting as a substrate for mammalian transglutaminases, comprising an antibody against a polypeptide comprising the amino acid sequence of SEQ. ID NO. 1 (or an antigenic portion thereof), wherein said polypeptide (or an antigenic portion thereof) is capable of acting as a substrate for mammalian transglutaminases. In a preferred embodiment, the diagnostic kit further comprises a detectable label selected from the group consisting of colorimetric, enzymatic, fluorescent and radioactive labels. In another preferred embodiment, the microorganism is a bacteria or yeast, preferably a yeast, and more preferably *C. albicans*.

Another aspect of the present invention is a method for detecting a microorganism expressing a protein capable of acting as a substrate for mammalian transglutaminases, comprising the steps of contacting a sample with an antibody against a polypeptide comprising the amino acid sequence of SEQ. ID NO. 1 (or an antigenic portion thereof), wherein said polypeptide (or an antigenic portion thereof) is capable of acting as a substrate for mammalian transglutaminases, and detecting any binding of said microorganism with said antibody. In a preferred embodiment, the antibody is immobilized to a solid support. In another preferred embodiment, the antibody is conjugated to a detectable label selected from the group consisting of colorimetric, enzymatic, fluorescent and radioactive labels.

Yet another aspect of the invention is a method of preventing or treating infection by a microorganism of a mammalian host, comprising the steps of administering syngeneic host cells transformed with the vector comprising DNA encoding the polypeptide of SEQ. ID NO. 1, wherein said transformed syngeneic host cells produce a protein capable of acting as a substrate for mammalian transglutaminases and inhibiting the interaction of said microorganism with the cells of said host. In a preferred embodiment, the transformed syngeneic host cells are capable of inhibiting the interaction of a microorganism with a mammalian cell, preferably where the microorganism is a bacteria or yeast, and more preferably where the microorganism is *C. albicans*. In one other preferred embodiment, the mammalian cell is a human cell, preferably an epithelial cell, more preferably a mucosal epithelial cell, and most preferably a buccal epithelial cell. In yet another preferred embodiment, the administering is performed orally. In a preferred embodiment, the mammalian host is immunocompromised, and in another, the infection is associated with AIDS.

Other objects, features and advantages of the present invention will become apparent from the following detailed description. The detailed description and the specific examples, however, indicate only preferred embodiments of the invention. Various changes and modifications within the spirit and scope of the invention will become apparent to those skilled in the art from this detailed description.

DESCRIPTION OF DRAWINGS

FIG. 1 (SEQ. ID NO. 1) represents the sequence of amino acids 40 to 187 encoded by HWP1 cDNA.

FIG. 3 depicts the disruption of HWP1. Panel A: Genomic HWP1 DNA showing the open reading frame (arrow), plasmid insert of pGBHWP1 (shaded rectangle), disruption fragment from pHWP1URA3 and the rescue fragment (1.7 kb).

Panel B: Southern blot analysis of genomic DNA digested with EcoRI and probed with the rescue fragment. Lanes 1 and 2, HWP1/HWP1 strains (3.8 kb); Lane 3, heterozygous hwp1/HWP1 strain (CAH7) (3.8, 5.3 and 2.3 kb). Lane 4, homozygous hwp1/hwp1 strain (CAH7-1A) (5.3, 5.1 kb doublet, and 2.3 kb). Lane 5, revertant strain CAHR3. Lane 6, UnoPP-1.

Panel C: Northern blot probed with HWP1 and ENO (internal control) showing the absence of HWP1 MRNA in CAH7-1A. Strains CAHR3 and CAH7 had levels of HWP1 MRNA approximately half those of SC5314 and UnoPP-1, strains with unaltered HWP1 genes (FIG. 3C). The abundance of HWP1 MRNA was quantitated with ImageQuant Software (Molecular Dynamics, Inc.).

FIG. 4 depicts transglutaminase-mediated incorporation of [$^{14}$C] putrescine by rHwp1$\Delta$C37, casein and BSA in Panel A. The values are the means±SD of two experiments performed in triplicate. Panel B: Autoradiograph of reactions with rHwp1$\Delta$C37, [$^{14}$C]-putrescine and transglutaminase (arrows) following SDS-PAGE and fluorography. Panel C: Inununoblot verifying rHwp1$\Delta$C37 in transglutaminase reactions. Affinity-purified antibodies against rHwp1 and horseradish peroxidase-conjugated goat anti-rabbit-antibodies (Zymed), developed with ECL reagents (Amersham). Lane 6, rHwp1$\Delta$C37 alone. TG: transglutaminase.

FIG. 5 depicts adherence to human buccal epithelial cells (BECs) of heterozygous hwp1/HWP1 (CAH7) and homozygous hwp1/hwp1 (CAH7-1A) mutants, and HWP1 revertant (CAHR3) relative to the homozygous HWP1/HWP1 strain (UnoPP-1). The adherence of each strain relative to UnoPP-1 was determined. The values are the means±SD of two experiments performed in duplicate. The Student's t test was used to determine statistically significant differences.

Panel A: Stabilized adhesion. "*" indicates the presence of iodoacetamide. CAH7-1A compared to CAH7 (P=0.009), CA7-1A compared to UnoPP-1 using iodoacetamide to inhibit transglutaminase (P=0.936), CAHR3 compared to CAH7 (P=0.977). Panel B: Overall adhesion. CAH7-1A compared to CAH7 (P=0.032), CAHR3 compared to CAH7 (P=0.513). Panel C: Phase-contrast photomicrographs of a BEC envelope (top) or a BEC (bottom) with adherent germ tubes of C. albicans strain UnoPP-1 germ tubes taken after separation on Percoll gradients. Heating to 100° C. in the presence of SDS produced BEC envelopes that were more transparent than BECs and lacked nuclei and surface particulates evident in BECs. Magnification—600×.

Figure 6:
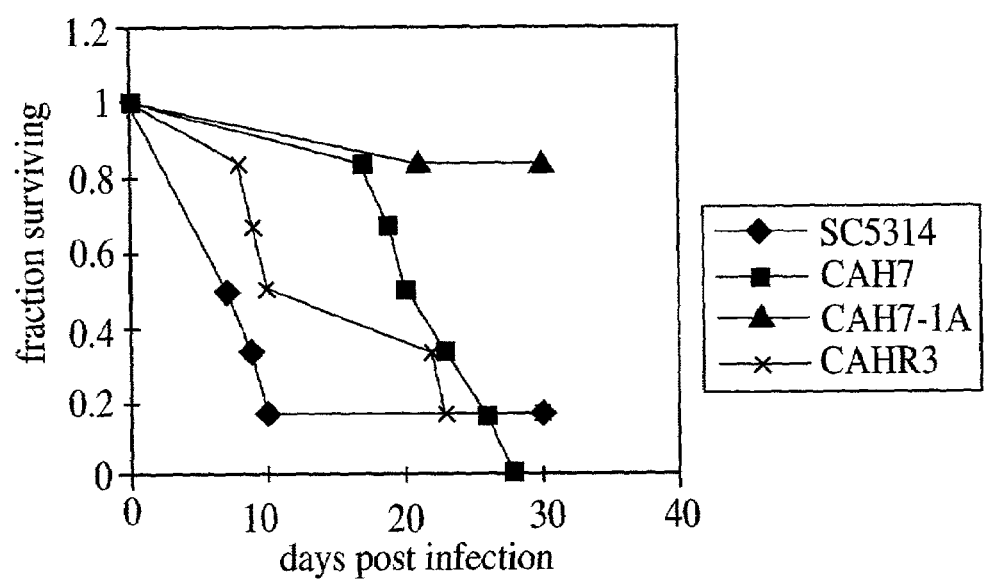

FIG. 6 depicts the survival of mice intravenously injected with HWP1 mutant strains. Four groups (6 mice/group) of mice (CBA/J H-$2^k$ haplotype) were inoculated intravenously with strains SC5314 (wild type), CAH7 (heterozygous hwp1/HWP1 mutant), CAH7-1A (homozygous hwp1/hwp1 mutant) or CAHR3 (revertant) with stationary phase yeast forms (34) ($2\times10^5$ blastoconidia/mouse in 0.2 ml PBS) of each strain. The experiment was terminated at 30 days. These studies were conducted in accordance with the NIH guidelines for the care and use of laboratory animals. The authenticity of strains taken from organs of infected mice was verified by assessment of the presence of Hwp1 on germ tubes by indirect immunofluorescence. The null hypothesis that survival for all groups was equivalent was proved false with $P<0.01$ by the Wilcoxin test. Survival of mice given CAH7-1A was significantly different from each of the other strains ($P<0.02$) using the log rank test for each comparison.

FIG. 7 (SEQ. ID NO. 2) represents a nucleotide sequence corresponding to amino acids 40 to 187 encoded by HWP1 cDNA.

DETAILED DESCRIPTION OF PREFERRED EMBODIMENTS

Transglutaminases are a family of enzymes that are $Ca^{2+}$ dependent and have thiol-containing active sites that form covalent $N^{68}$-($\gamma$-glutamyl)lysine isodipeptide bonds that are stable to denaturants such as urea, SDS and reducing agents. In squamous epithelial cells, transglutaminases catalyze the formation of rigid, cornified envelopes forming an impenetrable, first line host defense barrier. Buccal epithelial cell (BEC) transglutaminases cross-link salivary proline-rich proteins (PRPs) to proteins on BEC surfaces in a process that may affect mucosal pellicle function and counteract microbial adhesion.

While conformational constraints exist for the endoglutamine substrate protein, essentially any primary amine, such as putrescine, methylamine, cadaverine or free lysine can participate in cross-linking reactions. The conformational constraints within proteins that favor certain glutamine and lysine residues as substrates for cross-linking suggest a preference for terminal sequence regions, and/or sequences that are exposed on the protein surface. The envelope precursors that serve as substrates for epithelial cell transglutaminase are a heterogeneous group of proteins with conserved termini, including involucrin, cornifins, loricrin, small proline-rich proteins (SPRPs), for example.

Until now, it has been assumed that microbial adhesion is mediated-solely by noncovalent interactions with the host. The presence of a transglutaminase substrate on hyphal surfaces explains stabilized adhesion of C. albicans to BECs and provides a plausible explanation for earlier reports alluding to irreversible binding to BECs. The discovery of transglutaminase-mediated stabilized adhesion of C. albicans to oral squames implicates the significance of components of salivary pellicle and particularly salivary acidic proline-rich proteins (APRPs), as antagonists in transglutaminase-mediated interactions of C. albicans with mucosal surfaces.

APRPs, in combination with basic and neutral proline-rich proteins, constitute 70% of the proteins in parotid saliva. Multiple functions have been ascribed to APRPs that include detoxification of tannins, tooth remineralization, and serving as receptors for microorganisms. APRPs have proline and glutamine-rich regions. Certain APRPs are transglutaminase substrates and become covalently linked to BECs. The ability to cross-link APRPs to donor BECs from healthy adults suggests that the surface of oral epithelial squames is a partially denuded protein matrix replete with an associated transpeptidase which may cross-link appropriate substrates such as APRPs that come in contact with the cell surface. In addition, APRPs may function to resist stabilized adhesion of C. albicans by forming salivary pellicle and diminishing transglutaminase activity on the surfaces of oral squames.

The overall protective effect of saliva in resisting colonization is well supported by clinical studies. The association of xerostomia in HIV infected patients and others with candidiasis, as a result of treatment with didanosine or other factors, studies with cancer patients that have low levels of saliva, and animal studies support a role for anti-candidal factors in saliva. Other anti-fungal factors in saliva such as histatins and calprotectin are also likely to contribute to protection against candidiasis. Thus, transglutaminase-mediated interactions of salivary proteins with BECs might be one unrecognized component of the overall protective effect of saliva.

Given the complexity of the composition of saliva, it is important that mechanisms that deter microbial pathogen attachment and invasion be distinguished from those that promote microbial growth. For example, a basic proline-rich protein when applied to hydroxyapatite apparently promotes attachment of C. albicans. Other factors in saliva may also promote adherence and colonization by C. albicans.

Germ tubes and hyphae of C. albicans possess unique surface proteins that are not expressed in yeasts. Among these proteins is an outer mannoprotein, Hwp1, with a cell surface-exposed, ligand-binding domain at the N-terminus and with C-terminal features that confer covalent integration into the $\beta$-glucan of the cell wall. The primary amino acid sequence of the Hwp1 N-terminal domain shows general similarity to substrates of mammalian transglutaminases in the abundance of glutamine and proline residues, consecutive glutamine residues, and short amino acid repeats.

In accordance with the present invention, a substrate for mammalian transglutaminases refers to any purified or synthetic compound (or fragment thereof) that binds (covalently or noncovalently) to one or more mammalian transglutaminases. In a preferred embodiment, a substrate for mammalian transglutaminases can inhibit the binding of one or more mammalian transglutaminases to purified Hwp1 protein or a polypeptide comprising the amino acid sequence of SEQ. ID NO. 1 (FIG. 1), wherein said polypeptide is itself capable of acting as a substrate for mammalian transglutaminases. In addition, microbial interaction with a mammalian host can include attachment or adhesion to the host cell surface, invasion of host cells, and elaboration of toxins, for example. The involvement of pathogenic mechanisms or virulence factors of the microorganisms can result in deleterious or beneficial effect to the mammalian host or an asymptomatic or benign infection. In certain instances, this interaction can be nonspecific. In others, such microbial interaction involves the specific binding of the microorganism to a particular receptor or receptor complex expressed on the host cell surface. In turn, the binding event can trigger changes in the microorganism and/or the mammalian host cell, leading to the progression of infection.

In accordance with the present invention, a mammalian host preferably includes immunocompromised or immunosuppressed humans, for example, those having AIDS or undergoing transplantation or anti-cancer therapy. The invention also preferably relates to humans with primary or secondary immunodeficiencies (MERCK MANUAL 16th ed., Chapter 19 (1992), herein incorporated by reference). In addition to mammalian hosts in which the normal immune response has been compromised or suppressed, the invention relates to mammalian hosts in which the normal microbial flora has been disrupted, for example, because of disease (e.g. hereditary, metabolic, infiltrative, or hematologic), trauma (e.g., burn, splenectomy, anesthesia), surgical or clinical procedure (e.g., catheterization or introduction of artificial implants such as dentures), or chemical, radiation, or other immunosuppressive prophylaxis or treatment. Accordingly, the microbial infection of the present invention includes infections related to opportunistic as well as pathogenic microorganisms.

An embodiment of the invention is a purified polypeptide comprising the amino acid sequence of SEQ. ID NO. 1. As used herein, polypeptide refers to a linear series of amino acid residues connected to one another by peptide bonds between the alpha-amino groups and carboxy groups of adjacent amino acid residues. Additional covalent bonds between portions of the peptide are also present to restrain the conformation of the molecule, such as amide and disulfide bonds. When used herein, protein also refers to a linear series of amino acid residues connected one to the other as in a peptide. The term synthetic peptide means a chemically derived chain of amino acid residues linked together by peptide bonds that is free of naturally occurring proteins and fragments thereof.

The three-letter symbols used to represent the amino acid residues in the peptides of the present invention are those symbols commonly used in the art. The amino acid residues are preferred to be in the L isomeric form. However, residues in the D isomeric form may be substituted for any L-amino acid, as long as the desired functional property of inhibition of transglutaminase-mediated microbial interaction with a mammalian host is retained by the peptide. The three-letter symbols used herein refer to the following amino acids: Ser is serine; Ile is isoleucine; Gln is glutamine; Phe is phenylalanine; His is histidine; Trp is tryptophan; Lys is lysine; Asn is asparagine; Leu is leucine; Gly is glycine; Thr is threonine; Asp is aspartic acid; Arg is arginine; and Ala is alanine.

Polypeptides of the present invention may include any analog, fragment or chemical derivative of the polypeptides capable of inhibiting transglutaminase-mediated microbial interaction with a mammalian host. Polypeptides thus may include soluble peptides, Ig-tailed fusion peptides, members of random peptide libraries (see, e.g., Lam, K. S. et al., *Nature* 354:82–84 (1991); Houghten, R. et al., *Nature* 354: 84–86 (1991)), combinatorial chemistry-derived molecular library made of D-and/or L- configuration amino acids, and phosphopeptides (including members of random or partially degenerate, directed phosphopeptide libraries, see, e.g., Songyang, Z. et al., *Cell* 72:767–778(1993)).

Such polypeptides may include those derived from mammalian transglutaminases and those derived from mammalian transglutaminase substrates. The term analog refers to any polypeptide having an amino acid sequence, in comparison to the amino acid sequences of the polypeptides of the present invention, in which one or more amino acids have been substituted with other amino acids; where the substituted amino acids allow or require the polypeptide to assume the equilibrium conformation of the domain of the parent protein. Often, cysteine, lysine and glutamic acid will be used for their side chains which can form covalent linkages to restrict the conformation of a peptide.

In such amino acid sequences, one or more amino acids in the fundamental sequence may preferably be substituted with another amino acid(s), the charge and polarity of which is similar to that of the native amino acid, i.e., a conservative amino acid substitution, resulting in a silent change. Substitutes for an amino acid within the fundamental polypeptide sequence can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cyteine, cystine, tyrosine, asparagine, and glutamine; (4) neutral nonpolar (hydrophobic) amino acids such as alanine, leucine, isoleucine, valine, proline, phenylalanine, tryptophan, and methionine.

Conservative amino acid changes within the fundamental polypeptide sequence can be made by substituting one amino acid within one of these groups with another amino acid within the same group. The biologically functional equivalent peptides, polypeptides, and proteins contemplated herein may possess about 70% or greater sequence similarity, preferably about 80% or greater sequence similarity, and most preferably about 90% or greater sequence similarity, to the sequence of, or corresponding moiety within, the fundamental amino acid sequence.

The term analog shall also include any polypeptide which has one or more amino acids deleted from or added to an amino acid sequence of a mammalian transglutaminase substrate, but which still retains inhibitory activity against transglutaminase-mediated microbial interaction with a mammalian host. The term fragment shall refer to any shorter version of the polypeptides, wherein the fragment is capable of inhibiting transglutamninase-mediated microbial interaction with a mammalian host.

Antibodies of the present invention may include any polyclonal, monoclonal, humanized, anti-idiotypic, chimeric or single chain antibodies, and FAb, $F(ab')_2$ and FAb expression library fragments, and epitope-binding fragments thereof.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

Example 1a (Mammalian Transglutaminase Substrates on *C. Albicans*)

To detect germ tube surface proteins serving as glutamine donors in transglutaminase-catalyzed cross-linking reactions, a fluorescence assay using a biotinylated lysine analogue as the primary amine acceptor and liver transglutaminase was developed.

Washed M199-germinated *C. albicans* cells ($10^8$/ml), guinea pig liver transglutaminase (8.5 µg), and 5-(biotinamido)pentylamine (30 µM) (Pierce) were incubated in reaction buffer 1 (400 µl) (100 mM Tris-Cl pH 7.5, 5 mM $CaCl_2$, 1 mM DTT, 2 mM EDTA) for 15 minutes at 37° C. Reactions were stopped with EDTA (10 mM), germ tubes were washed with distilled water, spotted onto microscope slides, air dried, incubated with avidin-FITC (1:100) (Zymed) and BSA-rhodamine (1:30) (Difco) in PBS at 37° C., washed and examined by fluorescence microscopy.

Figure 2A:
FIG. 2 depicts the reactivity of germ tube surfaces of hwp1/hwp1 mutant and wild type strains of *C. albicans* with transglutaminase. Panels A and C: Homozygous HWP1/HWP1 strains (SC5314) and (CAI4). Panel B: SC5314 with 20 mM EGTA. Panel D: Heterozygous mutant hwp1/HWP1 (CAH7). Panel E: Homozygous mutant hwp/hwp1 (CAH7-1A). Panel F: HWP1 revertant (CAHR3) Magnification—400×.
Figure 2B:
Figure 2C:

Germ tubes of *C. albicans* SC5314 (wild type strain) and CAI4 (a ura3 mutant) showed strong fluorescence as a result of transglutaminase activity (FIGS. 2A, 2C). The assay was inhibited by EGTA (FIG. 2) and iodoacetamide as expected. These results are comparable to those obtained using incorporation of [$^{14}C$]-putrescine to detect transglutaminase substrates on germ tube surfaces.

Example 1b (Role of Hwp1 in Mammalian Transglutaminase-mediated Binding)

To determine if Hwp1 on germ tubes was responsible for the transglutaminase-mediated cross-linking of the biotinylated lysine analogue to hyphal surfaces, mutant strains lacking HWP1 were created.

A 365 base pair BglII-BclI fragment was deleted from pGBHWP1, a recombinant plasmid containing genomic HWP1 DNA in pBluescript SK-(Stratagene), and replaced with the hisG-URA3-hisG cassette from p5921 (W. A. Fonzi, M. Y. Irwin, *Genetics* 134:717–728 (1993)) to create pHWP1URA3. A $Ura^+$ heterozygous hwp1/HWP1 strain, CAH7, was created by transformation of the ura3 auxotrophic strain CAI4 (Fonzi, supra) by spheroplast transformation (M. B. Kurtz, M. W. Cortelyou, D. R. Kirsch, *Mol. Cell. Biol.* 6:142–149 (1986)) with HindIII-digested pHWP1URA3. A $Ura^+$ homozygous hwp1/hwp1 strain, CAH7-1A was created by transformation of a $Ura^+$ heterozygous hwp1/hwp1 strain, CAH7-1, that was derived from CAH7 following selection on 5-fluoroorotic acid (5-FOA)-containing medium (J. D. Boeke, F. Lacroute, G. R. Fink, *Genet.* 197:345–346 (1984)). An HWP1 revertant strain, CAHR3, was created by co-transformation of a $Ura^-$ homozygous hwp1/hwp1 strain, CAH7-1A1, with Hind III-digested pGBHWP1 and p24enura (P. Postlethwait, P. Sundstrom, *J. Bacteriol.* 177:1772–1779 (1995)) digested with Xba I-Xho I resulting in disruption of an enolase gene with URA3. Gene replacements at the HWP1 and enolase loci were confirmed by Southern blotting. Although CAHR3 contained excess HWP1 DNA, HWP1 mRNA levels were equivalent to those of CAH7 which contained a single HWP1 gene. The presence or absence of HWP1 in each strain was correlated with surface Hwp1 by indirect immunofluorescence assays.

Figure 2D:
Figure 2E:
Figure 2F:

HWP1 was disrupted by replacing 365 bp in the N-terminal coding region with a hisGURA3 cassette (FIGS. 3A, 3B). Homozygous hwp1/hwp1 strains lacked HWP1 mRNA (FIG. 3C) and Hwp1 on germ tube surfaces. An HWP1 revertant was prepared by complementation of a homozygous hwp1/hwp1 mutant strain with HWP1 creating CAHR3 (FIGS. 3A, 3B). Levels of CAHR3 MRNA were similar to those of the heterozygous hwp1/HWP1 strain CAH7 (FIG. 3C), whereas germ tube Hwp1 expression was indistinguishable from that of the other strains. Transglutaminase-mediated incorporation of a lysine analogue in the homozygous hwp1/hwp1 mutant strain CAH7-1A (FIG. 2E) was nearly absent as shown by the marked decrease in fluorescence compared to SC5314, CAI4, and CAH7 (FIGS. 2A, 2C, 2D). The existence of an additional, less effective transglutaminase substrate was suggested by the weak fluorescence of CAH7-1A. Transglutaminase substrate activity on germ tubes was regained upon complementation of a homozygous hwp1/hwp1 mutant strain with HWP1 (FIG. 2F). Endogenous transglutaminase activity of *C. albicans* was not detected in this assay or in broken cell walls. The marked decrease in fluorescence of the homozygous hwp1/hwp1 mutant strain showed that Hwp1 is the major substrate for transglutaminase on germ tube surfaces.

Example 1c (Mammalian Transglutaminase Binding Region of Hwp1)

To determine if the Hwp1 N-terminal domain is a transglutaminase substrate, rHwp1ΔC37 was tested for transglutarninase-mediated incorporation of the primary amine putrescine.

rHwp1ΔC37 (10 µg), N,N' dimethylcasein (50 µg)(Sigma) or BSA (50 µg) (Fraction V, Sigma) was incubated with 250 nCi (2.2–2.3 nmol) of [$^{14}C$]-putrescine (Amersham or DuPont/NEN,108–110 mCi/mmol) and transglutaminase (3.4 µg) in reaction buffer 2 (100 mM Tris-Cl pH 7.5, 20 mM $CaCl_2$, 1 mM DTT, 1 mM EDTA) for 30 minutes at 37° C. (total volume 25 µl). Filters spotted with each reaction (10 µl) were plunged into cold 10% TCA, successively washed in 10% and 5% cold TCA, rinsed in acetone, air dried and counted in scintillant (Amersham). Background counts were determined from reactions without acceptor protein.

Figure 4A:
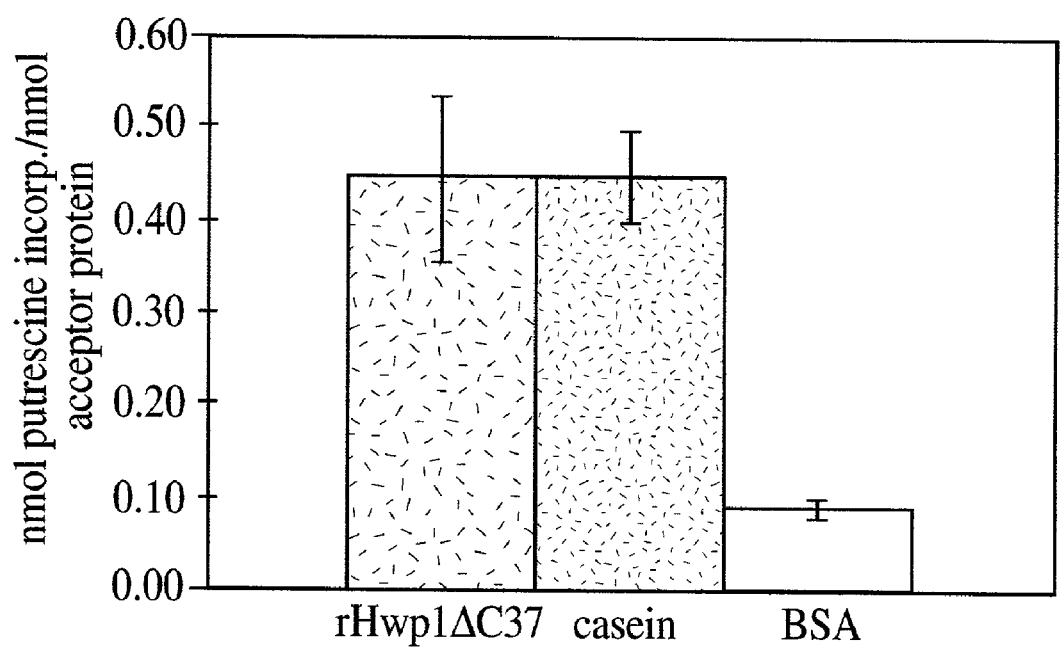

Incorporation of [$^{14}C$]-putrescine by rHwp1ΔC37 was equivalent to that of casein, a known substrate of transglutaminases (FIG. 4A). BSA served as a negative control.

rHwp1ΔC37 (10 µg) was incubated with 250 nCi [$^{14}C$] putrescine (108–110 mCi/mmol) and 3.4 µg of transglutaminase in 25 µl of reaction buffer 2, supra. Transglutaminase was inhibited with EGTA (20 mM) or iodoacetamide (20 mM). Reactions were incubated at 37° C. for 4 hrs., quenched with cold putrescine (100 mM) for one hour., and boiled in Laemmli sample buffer for 5 minutes. A portion of each sample was analyzed by SDS-PAGE followed by fluorography and exposure to x-ray film (Hyperfilm, Amersham) at −80° C. To visualize rHwp1ΔC37, immunoblotting using monospecific antiserum to rHwp1 was performed.

Figure 4B:
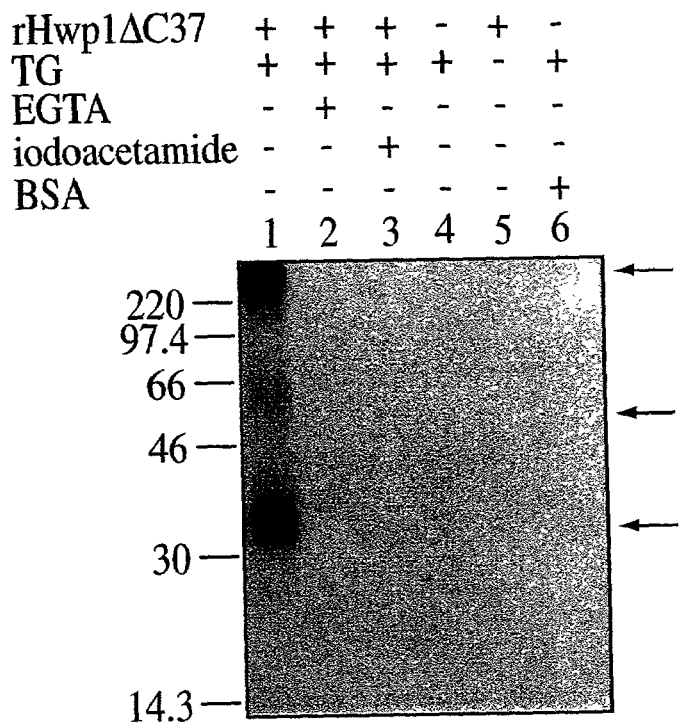

[$^{14}C$]-putrescine cross-linking to rHwp1ΔC37 detected by SDS-PAGE and fluorography required active transglutaminase and no evidence of cross-linking of [$^{14}C$]-putrescine to transglutaminase itself or to BSA was seen (FIG. 4B).

Figure 4C:
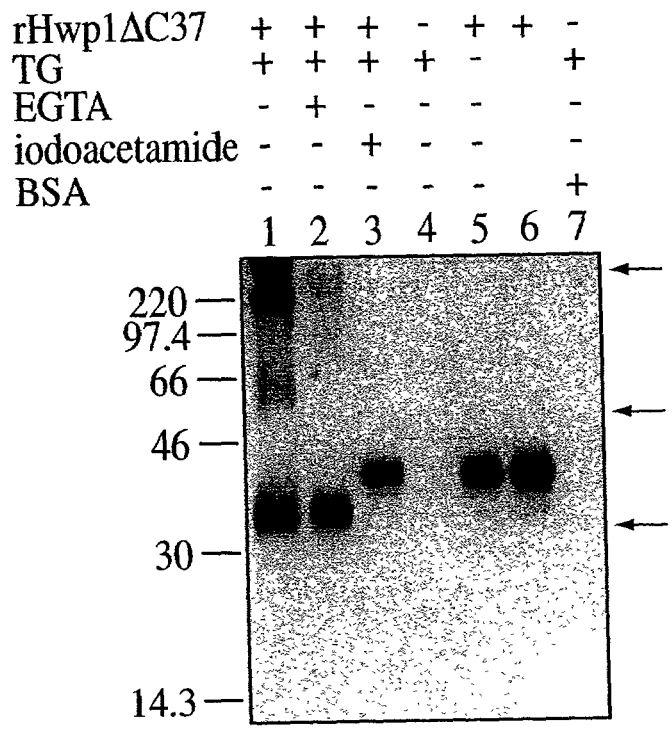

The presence of rHwp1ΔC37 in reactions was verified by immunoblotting (FIG. 4C). In addition to the monomer, aggregates of rHwp1ΔC37, which may result from the formation of putrescine bridges, were also radiolabeled and detected by immunoblotting. Taken together with the data in FIG. 2, the results show that the N-terminus of Hwp1 confers transglutaminase substrate properties to germ tube surfaces.

Example 1d (Hwp1 in Mammalian Transglutaminase-mediated Binding to Buccal Epithelial Cells)

Figure 5A:
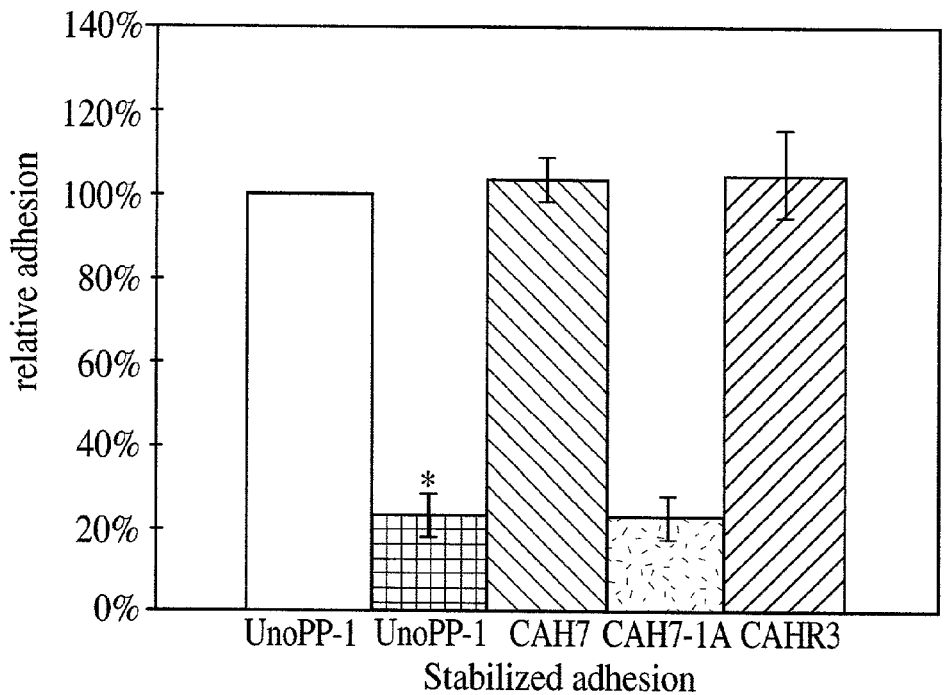
Figure 5B:
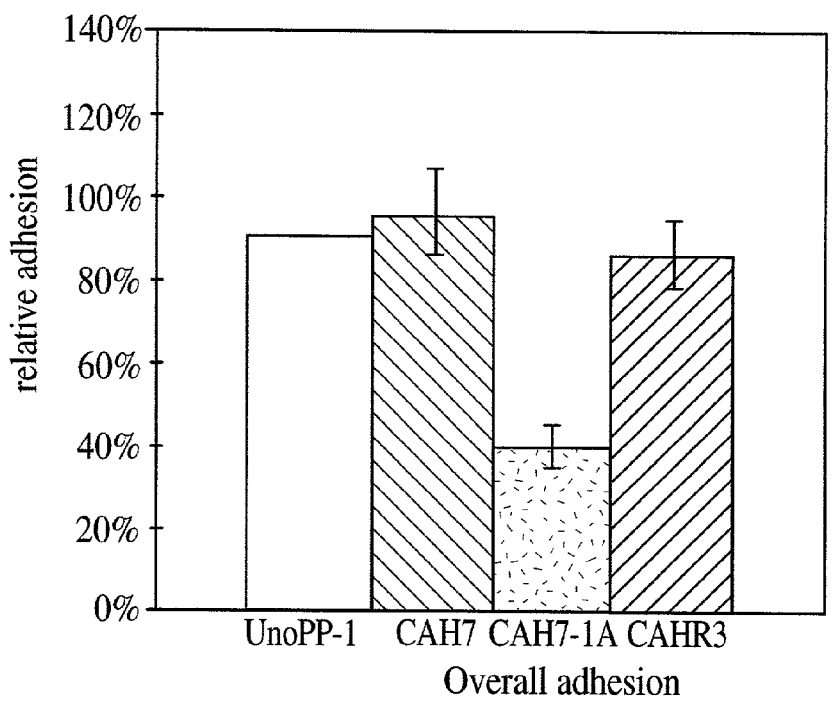
Figure 5C:
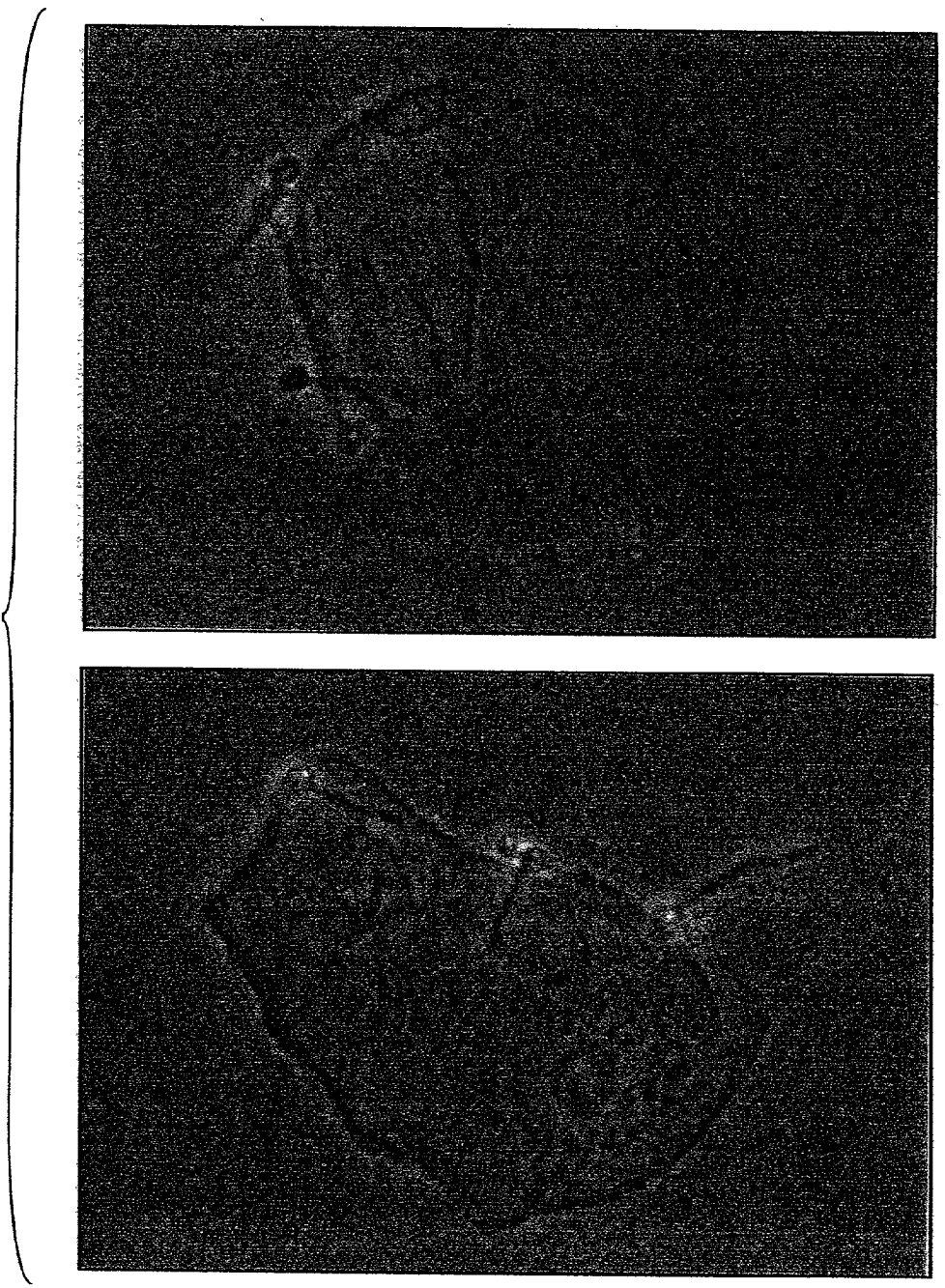

To determine if Hwp1 cross-links *C. albicans* germ tubes to buccal epithelial cells during incubation at 37° C., germtube-BEC complexes were heated to 100° C. in the presence of SDS, causing dissociation of noncovalent bonds, but leaving germ tubes and BEC envelopes intact (FIG. 5C, top panel).

Mass conversion of yeasts, radiolabeled with Tran$^{35}$S-label (ICN) (5 µCi/ml), to germ tubes (5×10$^6$/ml) was induced in prewarmed M199 (40 ml) for 2.5 hours at 37° C. No differences in the proportion of (>95%) germ tubes or in germ tube length were seen among strains. Washed germ tubes and BECs from a healthy donor, suspended in 300 µl of reaction buffer 3 (50 mM Tris-Cl pH 7.5, 10 mM CaCl$_2$, 1 mM EDTA, 1 mM DTT), at a germ tube/BEC ratio of 100:1, were mixed, incubated for 1 hour at 37° C. followed by reaction termination with 100 mM EGTA (75 µl). The BEC donors understood the nature of the studies and consented to provide BECs. Radioactivity of BEC fractions was determined by scintillation counting after centrifugation on 50% Percoll gradients, and germ tubes per BEC was determined using the specific activity of each strain. Background counts, determined from gradients with germ tubes only, were less than 6% of counts for germ tube/BEC mixtures and were subtracted from counts of epithelial cell-germ tube mixtures. For stabilized adhesion assays, reaction mixtures were heated to 100° C. for 2 minutes in PBS containing 1% SDS prior to loading on Percoll gradients. To inhibit transglutaminase, BECs were pretreated in PBS containing iodoacetamide (10 mM) for 15 minutes at 37° C., and suspended in reaction buffer supplemented with iodoacetamide (10 mM) prior to incubation with germ tubes.

UnoPP-1, a CAI4 derivative made Ura$^+$ by disruption of an enolase gene with URA3 and having unaltered HWP1 genes (FIGS. 3B, 3C), served as a positive control for HWP1 mutant strains that were also derived from CAI4 and contained URA3. Adherence of UnoPP-1 was set at 100%. Stabilized adhesion of the heterozygous hwp1/HWP1 strain CAH7 and the HWP1 revertant strain CAHR3 were indistinguishable from each other and from UnoPP-1 (FIG. 5A). However, stabilized adhesion of the hwp1/hwp1 mutant strain CAH7-1A was only 23% of UnoPP-1. The low level of stabilized adhesion of CAH7-1A was equivalent to that of UnoPP-1 when iodoacetamide was added to inhibit transglutaminase. These results show that C. albicans becomes cross-linked to epithelial cell envelopes and that Hwp1 is responsible for cross-linking.

Example 1e (Inhibition of the Adhesion of C. Albicans Germ Tubes to Human Buccal Epithelial Cells with Monodansylcadaverine)

Monodansylcadaverine is a primary amine that serves as a substrate for transglutaminases. In the presence of transglutaminase such as on BECs, monodansylcadaverine becomes cross-linked to substrates on C. albicans germ tubes thereby preventing linkage to primary amines on BECs.

Radiolabeled germ tubes of the control strain, UnoPP-1, were incubated with BECs at a ratio of 100:1 with or without 5 or 10 mM monodansylcadaverine in reaction buffer 3, supra. The monodansylcadaverine was added last to the reaction mix from a 100 mM stock solution prepared in DMSO and kept at room temperature, protected from light. An equal volume of DMSO was included in positive and background control tubes to assess any effects of DMSO on the adhesion assay. The cell mixtures were incubated for 1 hour at 37° C., and the number of germ tubes covalently attached to BECs were determined. The effect of monodansylcadaverine on the adhesion of germ tubes to BEC was determined relative to the control samples with DMSO alone. The inclusion of 5 or 10 mM monodansylcadaverine reduced the adhesion by approximately 87%, whereas DMSO alone had no effect on the adhesion of germ tubes to BEC. The ability to inhibit stabilized adhesion by monodansylcadaverine indicates the therapeutic usefulness of transglutaminase substrates in inhibition of adhesion of C. albicans to BECs.

Example 1f (Role of Hwp1 in the Adhesion of C. Albicans Germ Tubes to Human Buccal Epithelial Cells)

To determine if germ tubes lacking Hwp1 differed from other strains in the overall capacity to adhere to BECs, adhesion was measured following the standard 1 hour incubation at 37° C. Both covalent and non-covalent association of germ tubes with BECs contribute to overall adhesion. Covalent adhesion accounted for 35%±5.75% of overall adhesion of UnoPP-1 to BECs; the remainder resulting from non-covalent interactions. Overall adhesion of CAH7-1A was only 45% of UnoPP-1, whereas the heterozygous hwp1/HWP1 strain CAH7 and the HWP1 revertant strain CAHR3 were indistinguishable from each other and from UnoPP-1 (FIG. 5B). These results show that Hwp1 has a profound effect on the overall ability of C. albicans to adhere to BECs.

The results also suggest that Hwp1 contributes to non-covalent interactions with BECs. If Hwp1 were contributing only to covalent adhesion, the expected overall adhesion of CAH7-1A would be 65%. The observed overall adhesion of 45% relative to the other strains suggests that a portion of Hwp1 molecules do not become cross-linked to BECs during the 37° C. incubation. This result indicates that surface glycoproteins mediate adhesion by stereospecific and hydrophobic interactions. Hwp1 is thought to play a role in engaging the host surface with non-covalent adhesive domains that are subsequently stabilized by transglutaminase-catalyzed reactions. This potential multiplicity of adhesive mechanisms within Hwp1 increases the attractiveness of Hwp1 as a prophylactic or therapeutic target.

Example 1g (Hwp1 as a C. Albicans Virulence Factor)

The importance of Hwp1 in candidiasis is supported by experiments showing that the hwp1 mutant strain CAH7-1A has a greatly reduced capacity to cause systemic candidiasis in mice compared to strains expressing HWP1. Upon intravenous inoculation, five of six mice injected with the homozygous hwp1/hwp1 mutant strain CAH7-1A were alive at 30 days compared to only two of eighteen mice given HWP1-expressing strains (FIG. 6). Interestingly, the survival curve of the revertant closely approximated that of the wild type control SC5314, providing a clear role for Hwp1 in pathogenesis. Invasion associated with systemic candidiasis may be exacerbated through interactions of surface Hwp1 with a plasma transglutaminase, factor XIII or clot stabilizing factor. These results strongly implicate a central role for Hwp1 in the pathogenesis of transglutaminase-mediated infections such as candidiasis.

Example 2 (Polypeptide Substrates for Mammalian Transglutaminases)

The polypeptides of the present invention, such as the specific embodiment shown in FIG. 1 (SEQ. ID NO. 1) may be prepared by any known techniques. Conveniently, the polypeptides may be prepared using the solid-phase synthetic technique initially described by Merrifield in *J. Am. Chem. Soc.* 15:2149–2154 (1963). Other peptide synthesis techniques may be found, for example, in M. Bodanszky et al., PEPTIDE SYNTHESIS, John Wiley & Sons, 2d Ed. (1976) as well as in other reference works known to those skilled in the art. A summary of peptide synthesis techniques may be found in J. Stuart and J. D. Young, SOLID PHASE PEPTIDE SYNTHELIA, Pierce Chemical Co., Rockford, Ill. (1984). The synthesis of peptides by solution methods may also be used, as described in THE PROTEINS, Vol-II, 3d Ed., Neurath, H. et al., Eds., p. 105–237, Academic Press, New York, N.Y. (1976). Appropriate protective groups for use in such syntheses will be found in the above texts as well as in J. F. W. McOmie, PROTECTIVE GROUPS IN ORGANIC CHEMISTRY, Plenum Press, New York, N.Y. (1973). In general, these synthetic methods involve the sequential addition of one or more amino acid residues or suitably protected amino acid residues to a growing peptide chain. Normally, either the amino or carboxyl group of the first amino acid residue is protected by a suitable, selectively-removable protecting group. A different, selectively-removable protecting group is utilized for amino acids containing a reactive side group, such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The polypeptides of the invention preferably are devoid of benzylated or methylbenzylated amino acids. Such protecting group moieties may be used in the course of synthesis, but they are removed before the polypeptides are used. Additional reactions may be necessary, as described elsewhere to form intramolecular linkages to restrain conformation, if desired. The polypeptides of the present invention may also be linked to an additional sequence of amino acids either or both at the N-terminus and at the C-terminus. Such additional amino acid sequences, or linker sequences, can be conveniently affixed to a detectable label, solid matrix, or carrier. Typical amino acid residues used for linking are tyrosine, cysteine, lysine, glutamic acid and aspartic acid, or the like.

Of course, the present polypeptides may also be prepared by recombinant techniques. The present invention also relates to vectors comprising DNA molecules of the present invention, host cells which are genetically engineered with vectors of the invention and the production of polypeptides of the invention by recombinant techniques. Host cells may be genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying genes. The culture conditions, such as temperature, pH and the like, are preferably those previously used with the host cell selected for expression, and will be apparent to the skilled artisan.

Example 3 (DNA Encoding Polypeptide Substrates for Mammalian Transglutaminases)

The DNA molecule of the present invention may be employed for producing the polypeptides of the present invention by recombinant techniques. Thus, for example, the DNA molecule sequence may be included in any one of a variety of expression vehicles, in particular vectors or plasmids for expressing such a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA; viral DNA such as vaccinia, adenovirus, fowl pox virus, and pseudorabies. However, any other vector or plasmid may be used as long as they are replicable and viable in the host.

The appropriate DNA sequence may be inserted into the vector by a variety of procedures. In general, the DNA sequence is inserted into an appropriate restriction endonuclease sites by procedures known in the art. Such procedures and others are deemed to be within the scope of those skilled in the art.

The DNA sequence in the expression vector may be operatively linked to an appropriate expression control sequence(s) (promoter) to direct MRNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably may contain a gene to provide a phenotypic trait for selection of transformed host cells such as dihydrofolate reductase or neomycin resistance for eukaryotic cell culture, or such as tetracycline or ampicillin resistance in *E. coli*.

An embodiment of the invention is an isolated DNA molecule comprising the nucleotide sequence of SEQ. ID NO. 2 (FIG. 7). This nucleotide sequence, or fragments or functional equivalents thereof, may be used to generate recombinant DNA molecules that direct the expression of the polypeptides of the present invention, or functionally active peptides or functional equivalents thereof, in appropriate host cells. Due to the degeneracy of the nucleotide coding sequence, other DNA sequences which encode substantially the same amino acid sequences as depicted in SEQ. ID NO. 1, or analogs or fragments thereof, may be used in the practice of the invention for the cloning and expression of a substrate for mammalian transglutaminases. Such alterations include deletions, additions or substitutions of different nucleotide residues resulting in a sequence that encodes the same or a functionally equivalent gene product. The gene product may contain deletions, additions or substitutions of amino acid residues within the sequence, which result in a silent change thus producing a bioactive product. Such amino acid substitutions may be made on the basis of similarity in polarity, charge, solubility, hydrophobicity, hydrophilicity, the amphipathic nature of the residues involved and/or on the basis of crystallographic data. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine.

Techniques well known to those skilled in the art for the isolation of DNA, generation of appropriate restriction fragments, construction of clones and libraries, and screening recombinants may be used. For a review of such techniques, see, for example, Sambrook, et al., MOLECULAR CLONING: A LABORATORY MANUAL, Chapters 1–18, Second Edition (Cold Spring Harbor N.Y. 1989), the disclosure of which is hereby incorporated by reference. Also, the 5' untranslated and coding regions of the nucleotide sequence could be altered to improve the translational efficiency of the mRNA. In addition, based on X-ray crystallographic data, sequence alterations could be undertaken to improve protein stability, e.g., introducing disulfide bridges at the appropriate positions, and/or deleting or replacing amino acids that are predicted to cause protein instability. These are only examples of modifications that can be engineered to produce a more active or stable protein, more protein, or even change the substrate specificity of the protein.

Example 4 (Recombinant Vector Containing DNA Encoding Polypeptide Substrates for Mammalian Transglutaminases)

The vector containing the appropriate DNA sequence, as well as an appropriate promoter or control sequence, may be employed to transform an appropriate host to permit the host to express the polypeptides of the present invention. Representative examples of appropriate hosts include: bacterial cells, such as $E.\ coli,\ Salmonella\ typhimurium,\ Streptomyces$; fungal cells, such as yeast; insect cells, such as Drosophila S2 and Spodoptera Sf9; animal cells, such as CHO, COS or Bowes melanoma; adenoviruses; plant cells, etc. The selection of an appropriate host is deemed to be within the scope of those skilled in the art.

More particularly, the present invention also includes recombinant constructs comprising one or more of the sequences as broadly described above. The constructs may comprise a vector, such as a plasmid or viral vector, into which a sequence of the invention has been inserted, in a forward or reverse orientation. In a preferred aspect of this embodiment, the construct may further comprise regulatory sequences, including, for example, a promoter operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, phagescript, psiX174, pBluescript SK, pBsKS, pNH8a, pNH16a, pNH18a, pNH46a (Stratagene); pTRC99A, pKK223-3, pKK233-3, pDR540, PRIT5 (Pharmacia). Eukaryotic: pWLneo, pSV2cat, pOG44, pXT1, pSG (Stratagene); pSVK3, pBPV, pMSG, PSVL (Pharmacia). However, any other plasmid or vector may be used as long as they are replicable and viable in the host.

Suitable promoter regions can be selected from any desired gene using CAT (chloramphenicol transferase) vectors or other vectors with selectable markers. Two appropriate vectors are pKK232-8 and pCM7. Particular named bacterial promoters include laci, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of skill in the art.

Example 5 (Cells Transformed with Recombinant Vectors Containing DNA Encoding Polypeptide Substrates for Mammalian Transglutaminases)

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. The host cell preferably may secrete the recombinant protein. Introduction of the construct into the host cell can be effected by calcium phosphate transfection, DEAE-Dextran mediated transfection, or electroporation (L. Davis et al., BASIC METHODS IN MOLECULAR BIOLOGY, 1986)).

The constructs in host cells can be used in a conventional manner to produce the gene product encoded by the recombinant sequence. Alternatively, the polypeptides of the invention can be synthetically produced by conventional peptide synthesizers. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., supra.

Transcription of a DNA encoding the polypeptides of the present invention by higher eukaryotes may be increased by inserting an enhancer sequence into the vector. Enhancers are cis-acting elements of DNA, usually from about 10 to 300 bp, that act on a promoter to increase its transcription. Examples include the SV40 enhancer on the late side of the replication origin (base pair 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of $E.\ coli$ and $S.\ cerevisiae$ TRP1 gene, and a promoter derived from a highly-expressed gene to direct transcription of a downstream structural sequence. Such promoters can be derived from operons encoding glycolytic enzymes such as 3-phosphoglycerate kinase (PGK), alpha factor, acid phosphatase, or heat shock proteins, among others. The heterologous structural sequence is preferably assembled in appropriate phase with translation, initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use may be constructed by inserting a structural DNA sequence encoding a desired protein together with suitable translation, initiation and termination signals in operable reading phase with a functional promoter. The vector may comprise one or more phenotypic selectable markers and an origin of replication to ensure maintenance of the vector and to, if desirable, provide amplification within the host. Suitable prokaryotic hosts for transformation include $E.\ coli,\ Bacillus\ subtilis,\ Salmonella\ typhimurium$ and various species within the genera $Pseudomonas,\ Streptomyces$, and $Staphylococcus$, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis.). These pBR322 backbone sections are combined with an appropriate promoter and the structural sequence to be expressed.

Following transformation of a suitable host strain and growth of the host strain to an appropriate cell density, the selected promoter may be de-repressed by appropriate means (e.g., temperature shift or chemical induction) and cells may be cultured for an additional period. Cells are typically harvested by centrifgation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents. Various mammalian cell culture systems can also be employed to express recombinant polypeptides. Examples of mammalian expression systems include the COS-7 lines of monkey kidney fibroblasts, described by Gluzman, *Cell,* 23:175 (1981), and other cell lines capable of expressing a compatible vector, for example, the C127, 3T3, CHO, HeLa and BHK cell lines. Mammalian expression vectors may comprise an origin of replication, a suitable promoter and enhancer, and also any necessary ribosome binding sites, polyadenylation sites, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

The polypeptides of the present invention may be recovered and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic-procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue.

Example 6 (Pharmaceutically Acceptable Salts of Polypeptide Substrates for Mammalian Transglutaminases)

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfirric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, and the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanolamines (e.g., ethanolamine, diethanolamine and the like).

Example 7 (Pharmaceutical Compositions Containing Polypeptide Substrates for Mammalian Transglutaminases)

For use in a method of identification, prevention or treatment, such as the identification, prevention or treatment of infection of a mammalian host by a microorganism, the polypeptides of the present invention may be present in a pharmaceutical composition in admixture with a pharmaceutically acceptable sterile vehicle. The pharmaceutical composition may be compounded according to conventional pharmaceutical formulation techniques.

The vehicle may take a wide variety of forms depending on the form of preparation desired for administration, e.g., sublingual, rectal, nasal, oral or parenteral. Compositions for oral dosage form may include any of the usual pharmaceutical media, such as, for example, water, oils, alcohols, flavoring agents, preservatives, coloring agents and the like in the case of oral liquid preparations (e.g., suspensions, elixirs and solutions) or carriers such as starches, sugars, diluents, granulating agents, lubricants, binders, disintegrating agents and the like in the case of oral solid preparations (e.g., powders, capsules and tablets). Controlled release forms may also be used. Because of their ease in administration, tablets and capsules represent an advantageous oral dosage unit form, in which case solid pharmaceutical carriers may be employed. If desired, tablets may be sugar coated or enteric coated by standard techniques.

For compositions to be administered parenterally, the carrier will usually comprise sterile water, although other ingredients to aid solubility or for preservation purposes may be included. Injectable suspensions may also be prepared, in which case appropriate liquid carriers, suspending agents and the like may be employed. The parenteral routes of administration may be intravenous injection, intramuscular injection or subcutaneous injection.

For intravenous administration, the polypeptides may be dissolved in an appropriate intravenous delivery vehicle containing physiologically compatible substances such as sodium chloride, glycine and the like, having a buffered pH compatible with physiologic conditions. Such intravenous delivery vehicles are known to those skilled in the art.

The polypeptides of the invention may be administered to subjects where inhibition of transglutaminase-mediated microbial interaction with a mammalian host is desired. The peptides may be administered by any convenient means that will result in the delivery to the subject of an effective amount to inhibit transglutaminase-mediated microbial interaction with a mammalian host. Oral administration is presently contemplated as a preferred administration route. The amount administered will depend on the activity of the particular compound administered, which may readily be determined by those of ordinary skill in the art.

Example 8 (Monoclonal Antibodies against Polypeptide Substrates for Mammalian Transglutaminases)

Another embodiment of the present invention relates to a monoclonal antibody to the polypeptides of the present invention (or an antigenic portion thereof), which may be produced by methods recognized in the art, including the formation of monoclonal antibody-producing hybridomas (Kohler, G., and C. Milstein, *Nature* 256:495–497 (1975); *Eur. J. Immunol.* 6:511–519 (1976)). By fusing antibody-forming cells (spleen lymphocytes) with myeloma cells (malignant cells of bone marrow primary tumors), a hybrid cell line is created from a single fused cell hybrid (called a hybridoma or clone) having certain inherited characteristics of both the lymphocytes and myeloma cell lines. Like the lymphocytes (taken from animals primed with sheep red blood cells as antigen), the hybridomas secreted a single type of immunoglobulin specific to the antigen; moreover, like the myeloma cells, the hybrid cells had the potential for indefinite cell division. The combination of these two features offered distinct advantages over conventional antisera. Whereas antisera derived from vaccinated animals are variable mixtures of polyclonal antibodies which never can be reproduced identically, monoclonal antibodies are highly specific immunoglobulins of a single type. The single type of immunoglobulin secreted by a hybridoma is specific to one and only one antigenic determinant, or epitope, on the antigen, a complex molecule having a multiplicity of antigenic determinants. For instance, if the antigen is a protein, an antigenic determinant may be one of the many peptide sequences (generally 6–7 amino acids in length (Atassi, M. Z., *Molec. Cell. Biochem.* 32:21–43 (1980)) within the entire protein molecule. Hence, monoclonal antibodies raised against a single antigen may be distinct from each other depending on the determinant that induced their formation; but for any given clone, all of the antibodies it produces are identical. Furthermore, the hybridoma cell line can be reproduced indefinitely, is easily propagated in vitro or in vivo, and yields monoclonal antibodies in extremely high concentration.

Example 9 (Therapeutic Monoclonal Antibodies against Polypeptide Substrates for Mammalian Transglutaminases)

The monoclonal antibodies of the present invention can have potential immunotherapeutic value (Oldham, R. K., *J. Clin. OncoL,* 1:582–590 (1983); Miller, R. A. et al., *Blood,* 62:988–995 (1983); Miller R. A. et al., *New Engl. J. Med.* 306:517–522 (1982); Ritz, J. and Schlossman, S., *Blood,* 59:1–11 (1982); and Kirch, M. E. and Ulrich, H., *J. Immunol.* 127:805–810 (1981) (investigating the therapeutic efficacy in both animal and human subjects)). In addition, the monoclonal antibodies can be used in cytotoxic drug-antibody conjugates similar to those described in Beverly, P. C. L., *Nature,* 297:358–9 (1982); Krolick, K. A. et al., *Nature,* 295:604–5 (1982); Krolick, K. A. et al., *Proc. Natl. Acad. Sci. U.S.A.,* 77:5419–23 (1980); Arnon, R. and Sela, M., *Immunol. Rev.,* 62:5–27 (1982); Raso, V. et al., *Cancer Res.,* 42:457–64 (1982); and DeWeger, R. A. and Dullens, H. F. J., *Immunol. Rev.* 62:29–45 (1982).

In an embodiment of the invention, purified polypeptides of the present invention (or an antigenic portion thereof) can be used as an antigen or immunogen. In addition, microorganisms expressing Hwp1 protein or polypeptide fragments thereof also represent potential antigens or sources of antigen with which to immunize animals to obtain somatic cells for fusion. Somatic cells with the potential for producing antibody and, in particular, B lymphocytes, are suitable for fusion with a B-cell myeloma line. Those antibody-producing cells that are in the dividing plasmablast stage fuse preferentially. Somatic cells may be derived from the lymph nodes, spleens and peripheral blood of primed animals and the lymphatic cells of choice depending to a large extent on their empirical usefulness in the particular fusion system. Once-primed or hyperimmunized animals can be used as a source of antibody-producing lymphocytes. Mouse lymphocytes give a higher percentage of stable fusions with mouse myeloma lines. However, the use of rat, rabbit, and frog cells is also possible. Alternatively, human somatic cells capable of producing antibody, specifically B lymphocytes, are suitable for fusion with myeloma cell lines. While B lymphocytes from biopsied spleens or lymph nodes of individual may be used, the more easily accessible peripheral blood B lymphocytes are preferred. The lymphocytes may be derived from patients with diagnosed carcinomas.

Specialized myeloma cell lines have been developed from lymphocyte tumors for use in hybridoma-producing fusion procedures (Kohler, G., and C. Milstein, *Eur. J. Immunol.* 6:511–519 (1976); M. Schulman et al., *Nature* 276: 269–270 (1978)). Examples of myeloma cell lines that may be used for the production of fused cell hybrids include X63-Ag8, NSI-Ag4/1, MPC11-45.6TG1.7, C63-Ag8.653, Sp2/0-Ag14, FO, and S194/5XX0.BU.1, all derived from mice; 210.RCY3.Ag1.2.3, U-226AR, and GM1500GTGAL2, all derived from rats; and U-226AR and GM1500GTGAL2, derived from humans, (G. J. Hammerling, U. Hammerling, and J. F. Kearney (editors), *Monoclonal Antibodies and T-cell Hybridomas* in: J. L. Turk (editor) RESEARCH MONOGRAPHS IN IMMUNOLOGY, Vol. 3, Elsevier/North Holland Biomedical Press, NY (1981)).

Methods for generating hybrids of antibody-producing spleen or lymph node cells and myeloma cells usually comprise mixing somatic cells with myeloma cells in a 2:1 proportion (though the proportion may vary from about 20:1 to about 1:1), respectively, in the presence of an agent or agents (chemical or electrical) that promote the fusion of cell membranes. It is often preferred that the same species of animal serve as the source of the somatic and myeloma cells used in the fusion procedure. Fusion methods have been described by Kohler and Milstein (*Nature* 256:495–497 (1975) and *Eur. J. Immunol.* 6:511–519 (1976), and by Gefter et al. (*Somatic Cell Genet.* 3:231–236 (1977)). The fusion-promotion agents used by those investigators were Sendai virus and polyethylene glycol (PEG), respectively.

Generally, the fused cells are cultured in selective media, for instance HAT medium containing hypoxanthine, aminopterin and thymidine. HAT medium permits the proliferation of hybrid cells and prevents growth of unfused myeloma cells which normally would continue to divide indefinitely. Aminopterin blocks de novo purine and pyrimidine synthesis by inhibiting the production of tetrahydrofolate. The addition of thymidine bypasses the block in pyrimidine synthesis, while hypoxanthine is included in the media so that inhibited cells synthesize purine using the nucleotide salvage pathway. The myeloma cells employed are mutants lacking hypoxanthine phosphoribosyl transferase (HPRT) and thus cannot utilize the salvage pathway. In the surviving hybrid, the B lymphocyte supplies genetic information for production of this enzyme. Since B lymphocytes themselves have a limited life span in culture (approximately two weeks), the only cells which can proliferate in HAT media are hybrids formed from myeloma and spleen cells.

To facilitate screening of antibody secreted by the hybrids and to prevent individual hybrids from overgrowing others, the mixture of fused myeloma and B lymphocytes is diluted in HAT medium and cultured in multiple wells of microtiter plates. In two to three weeks, when hybrid clones become visible microscopically, the supernatant fluid of the individual wells containing hybrid clones is assayed for specific antibody. The assay is preferably sensitive, simple and rapid. Assay techniques include radioimmunoassays, enzyme immunoassays, cytotoxicity assays, plaque assays, dot immunobinding assays, and the like.

Once the desired fused cell hybrids have been selected and cloned into individual antibody-producing cell lines, each cell line may be propagated in either of two standard ways. A sample of the hybridoma can be injected into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels; the culture medium, also containing high concentrations of a single specific monoclonal antibody, can be harvested by decantation, filtration or centrifugation.

Example 10 (Diagnostic Monoclonal Antibodies against Polypeptide Substrates for Mammalian Transglutaminases)

The monoclonal antibodies of this invention can be used as probes in detecting discrete antigens expressed by microorganisms. The expression or lack of expression of these antigens can provide clinically exploitable information that is not apparent after standard histopathological evaluations. It may thus be possible to correlate the immuno-phenotypes of individual microorganisms with various aspects of microbial-mammalian host interaction and responsiveness to certain types of therapies, thereby establishing important classifications of prognosis.

The antibodies may also be used to detect drug resistance in microorganisms. For example, drug resistant C. albicans can make hyphae (germ tubes) in the presence of drug, but susceptible strains cannot. See J. Gen Microbiol 138:1901–1911 (1992). Because Hwp1 is a marker of hyphae formation, the detection of the presence or absence of Hwp1 may be useful in the monitoring of drug resistance in C. albicans.

The use of the monoclonal antibodies described herein can be extended to the screening of human biological fluids for the presence of the specific antigenic determinant recognized. In vitro immunoserological evaluation of sera withdrawn from patients thereby permits non-invasive diagnosis of microbial infection. By way of illustration, human fluids, such as pleural fluids or lymph, can be taken from a patient and assayed for the specific epitope, either as released antigen or membrane-bound on cells in the sample fluid, using monoclonal antibodies of the present invention against the polypeptides of the present invention in standard radioimmunoassays or enzyme-linked immunoassays known in the art or competitive binding enzyme-linked immunoassays.

The monoclonal antibodies of this invention are potentially useful for targeting microbial infection in vivo. They can therefore be used in humans for localization and monitoring of the microbial infection. For this application, it is preferable to use purified monoclonal antibodies. Purification of monoclonal antibodies for human administration by ammonium sulfate or sodium sulfate precipitation followed by dialysis against saline and filtration sterilization has been described by Miller et al. (in: HYBRIDOMAS IN CANCER DIAGNOSIS AND THERAPY, (1982), p. 134).

Alternatively, immunoaffinity chromatography techniques may be used to purify the monoclonal antibodies. The purified monoclonal antibodies can be labeled with radioactive compounds, for instance, radioactive iodine, and administered to a patient intravenously. After localization of the antibodies at the infection site, they can be detected by emission tomographical and radionuclear scanning techniques, thereby pinpointing the location of the infection. Experimental radioimmunodetection with monoclonal antibodies may occur by external scintigraphy.

Passive monoclonal serotherapy may be a potential use for the monoclonal antibodies of this invention. By way of illustration, purified anti-Hwp1 monoclonal antibody is dissolved in an appropriate carrier, e.g., saline, with or without human albumin, at an appropriate dosage and is administered to a patient. The monoclonal antibodies are preferably administered intravenously, e.g., by continuous intravenous infusion over several hours, as in Miller et al, supra. Infusions can be administered over a period of weeks during which the anti-microbial effects are monitored.

Example 11 (Anti-idiotypic Antibodies to Antibodies against Polypeptide Substrates for Mammalian Transglutaminases)

In an alternate embodiment, the antibodies described herein are used to stimulate the production of corresponding anti-idiotypic antibodies. In brief, anti-idiotypic antibodies, or antiidiotypes are antibodies directed against the antigen combining region or variable region (idiotype) of another antibody. Based on Jerne's network model of idiotypic relationships (Jerne, Ann. Immunol. 125:373 (1974); Jerne et al., EMBO 1:234 (1982)), immunization with an antibody molecule expressing a paratope (antigen-combining site) for a given antigen should produce a group of anti-antibodies, some of which share with the antigen a complementary structure to the paratope. Immunization with a subpopulation of antiidiotypic antibodies should in turn produce a subpopulation of antiidiotypic antibodies which bind the initial antigen. Thus, the administration of the monoclonal antibodies of the present invention may result in a modification of the host's anti-microbial immune response, as the consequence of the formation of anti-idiotypic antibodies which may develop during therapy with the monoclonals.

Example 12 (Monoclonal Antibody-drug Conjugates)

The monoclonal antibodies of this invention can be used in conjunction with a broad spectrum of pharmaceutical or cytotoxic agents that selectively affect a microorganism over the mammalian host. The methods used for binding the cytotoxic agents to the monoclonal antibody molecule can involve either non-covalent or covalent linkages. Since non-covalent bonds are more likely to be broken before the antibody complex reaches the target site, covalent linkages are preferred. For instance, carbodiimide can be used to link carboxy groups of the pharmaceutical agent to amino groups of the antibody molecule. Bifunctional agents such as dialdehydes or imidoesters can be used to link the amino group of a drug to amino groups of the antibody molecule. The Schiff base reaction can be used to link drugs to antibody molecules. This method involves the periodate oxidation of a drug or cytotoxic agent that contains a glycol or hydroxy group, thus forming an aldehyde that is then reacted with the antibody molecule. Attachment occurs via formation of a Schiff base with amino groups of the antibody molecule. Additionally, drugs with reactive sulfhydryl groups have been coupled to antibody molecules.

Example 13 (Diagnostic Kit)

Another embodiment of the invention relates to a diagnostic kit for detecting a microorganism expressing a protein capable of acting as a substrate for mammalian transglutaminases using an antibody against the substrate. The diagnostic kit may further comprise, where necessary, other components of the signal producing system, including agents for reducing background interference, control reagents, or an apparatus, container or other solid support for conducting the test. The binding of antibody to the target can be detected by well known methods, including radiation (e.g., use of a radioactive nucleotide), colorimetry (e.g., use of an enzyme that can cause a color change in a substrate), fluorescence (e.g., use of a dye such as propidium iodide, fluorescein, or rhodamine), and luminescence (e.g., use of an alkaline phosphatase substrate that releases photons upon cleavage or luciferin). Detection can be qualitative or quantitative.

Example 14 (Gene Therapy)

Another embodiment of the present invention involves the use of the DNA of the present invention in gene therapy applications. Gene therapy has been broadly defined as "the correction of a disease phenotype through the introduction of new genetic information into the affected organism" (Roemer, K. and Friedmann, T., *Eur. J. Biochem.* 208: 211–225 (1992)). Two basic approaches to gene therapy have evolved: (1) ex vivo gene therapy and (2) in vivo gene therapy. In ex vivo gene therapy, cells are removed from a subject and cultured in vitro. A functional replacement gene is introduced into the cells (transfection) in vitro, the modified cells are expanded in culture, and then reimplanted in the subject. These genetically modified, reimplanted cells are reported to secrete detectable levels of the transfected gene product in situ (Miller, A. D., *Blood* 76: 271–278 (1990)) and Selden, R. F., et al., *New Eng. J. Med.* 317: 1067–1076 (1987)). The development of improved retroviral gene transfer methods (transduction) facilitates the transfer into and subsequent expression of genetic material by somatic cells (Cepko, C. L., et al., *Cell* 37: 1053–1062 (1984)). Accordingly, retrovirus-mediated gene transfer has been used in clinical trials to mark autologous cells and as a way of treating genetic disease (Rosenberg, S. A., et al., *New Eng. J. Med.* 323: 570–578 (1990); Anderson, W. F., *Human Gene Therapy* 2: 99–100 (1991)). Several ex vivo gene therapy studies in humans are reported (reviewed in Anderson, W. F., *Science* 256: 808–813 (1992) and Miller A. D., *Nature* 357: 455–460 (1992)).

In in vivo gene therapy, target cells are not removed from the subject. Rather, the transferred gene is introduced into cells of the recipient organism in situ, that is, within the recipient. In vivo gene therapy has been examined in several animal models (reviewed in Felgner, P. L. and Rhodes, G., *Nature* 349: 351–352 (1991)). Publications have reported the feasibility of direct gene transfer in situ into organs and tissues such as muscle (Ferry, N., et al, *Proc. Natl. Acad. Sci.* 88: 8377–8781 (1991); Quantin, G., et al., *Proc. Natl. Acad. Sci. USA* 89: 2581–2584 (1992)), hematopoietic stem cells (Clapp, D. W., et al, *Blood* 78: 1132–1139 (1991)), the arterial wall (Nabel, E. G., et al., *Science* 244: 1342–1344 (1989)), the nervous system (Price, J. D., et al., *Proc. Natl. Acad. Sci.* 84: 156–160 (1987)), and lung (Rosenfeld, M. A., et al., *Science* 252: 431–434 (1991)). Direct injection of DNA into skeletal muscle (Wolff, J. A., et al., *Science* 247: 1465–1468 (1990)), heart muscle (Kitsis, R. N., et al., *Proc. Natl. Acad. Sci. USA* 88: 4138–4142 (1991)) and injection of DNA-lipid complexes into the vasculature (Lim, C. S., et al., *Circulation* 83: 2007–2011 (1991); Ledere, G. D., et al., *J. Clin. Invest.* 90: 936–944 (1992); Chapman, G. D., et al., *Circ. Res.* 71: 27–33 (1992)) also have been reported to yield a detectable expression level of the inserted gene product(s) in vivo.

Recent gene therapy efforts have been aimed at the identification of various cell types for transformation, including keratinocytes (Morgan, J. R., et al., *Science* 237: 1476–1479 (1987)), fibroblasts (Palmer, T. D., et al., *Proc. Natl. Acad. Sci.* 88: 1330–1334 (1991); Garver Jr., R. I., et al., *Science* 237: 762–764 (1987); International Patent Application PCT/US92/01890, having publication number WO 92/15676), lymphocytes (Reimann, J. K., et al., *J. Immunol. Methods* 89: 93–101 (1986)), myoblasts (Barr, E. and Leiden, J. M., *Science* 254: 1507–1509 (1991); Dai, Y. et al., *PNAS* 89: 10892–10895 (1992); Roman, M., et al., *Somatic Cell and Molecular Genetics* 18: 247–258 (1992)), smooth muscle cells (Lynch, C. M. et al., *Proc. Natl. Acad. Sci. USA* 89: 1138–1142 (1992)), and epithelial cells (Nabel, E. G., et al., *Science* 244: 1342–1344 (1989)), International Patent Application PCT/US89/05575 (having publication number WO 90/06997), the contents of which references and patent/patent applications are incorporated herein by reference.

The delivery of an effective dose of a prophylactic or therapeutic agent in situ depends on the efficiency of transfection (or transduction) as well as the number of target cells. Epithelial cell-based gene therapy, in particular, involves a relatively small area available in situ for receiving genetically modified epithelial cells. The delivery of an effective dose of prophylactic or therapeutic agent in situ thus depends upon the total number of implanted epithelial cells.

In one embodiment of the invention, exogenous genetic material (e.g., a cDNA encoding a polypeptide of the present invention) is introduced into a syngeneic host cell ex vivo or in vivo by genetic transfer methods, such as transfection or transduction, to provide a genetically modified host cell. Various expression vectors (i.e., vehicles for facilitating delivery of exogenous genetic material into a target cell) are known to one skilled in the art.

Transfection refers to the insertion of nucleic acid into a mammalian host cell using physical or chemical methods. Several transfection techniques are known to those of ordinary skill in the art including: calcium phosphate DNA co-precipitation (METHODS IN MOLECULAR BIOLOGY, Vol. 7, *Gene Transfer and Expression Protocols*, Ed. E. J. Murray, Humana Press (1991)); DEAE-dextran; electroporation; cat-ionic liposome-mediated transfection; and tungsten particle-facilitated microparticle bombardment (Johnston, S. A., *Nature* 346: 776–777 (1990)). Strontium phosphate DNA co-precipitation (Brash D. E. et al. *Molec. Cell. Biol.* 7: 2031–2034 (1987)) is a preferred transfection method.

In contrast, transduction refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous genetic material contained within the retrovirus is incorporated into the genome of the transduced host cell. A host cell that has been transduced with a chimeric DNA virus (e.g., an adenovirus carrying a cDNA encoding a therapeutic agent) will not have the exogenous genetic material incorporated into its genome, but will be capable of expressing the exogenous genetic material that is retained extrachromosomally within the cell.

Typically, the exogenous genetic material includes the heterologous gene (usually in the form of a cDNA comprising the exons coding for the therapeutic protein) together with a promoter to control transcription of the new gene. The promoter characteristically has a specific nucleotide sequence necessary to initiate transcription. Optionally, the exogenous genetic material further includes additional sequences (i.e., enhancers) required to obtain the desired gene transcription activity. For the purpose of this discussion an enhancer is simply any non-translated DNA sequence which works contiguous with the coding sequence (in cis) to change the basal transcription level dictated by the promoter. Preferably, the exogenous genetic material is introduced into the host cell genome immediately downstream from the promoter so that the promoter and coding sequence are operatively linked so as to permit transcription of the coding sequence. A preferred retroviral expression vector includes an exogenous promoter element to control transcription of the inserted exogenous gene. Such exogenous promoters include both constitutive and inducible promoters.

Naturally-occurring constitutive promoters control the expression of essential cell functions. As a result, a gene under the control of a constitutive promoter is expressed under all conditions of cell growth. Exemplary constitutive promoters include the promoters for the following genes which encode certain constitutive or housekeeping functions: hypoxanthine phosphoribosyl transferase (HPRT), dihydrofolate reductase (DHFR) (Scharfmann et al., *Proc. Natl. Acad. Sci. USA* 88: 4626–4630 (1991)), adenosine deaminase, phosphoglycerol kinase (PGK), pyruvate kinase, phosphoglycerol mutase, the beta-actin promoter (Lai et al., *Proc. Natl. Acad. Sci. USA* 86: 10006–10010 (1989)), and other constitutive promoters known to those of skill in the art. In addition, many viral promoters function constitutively in eukaryotic cells. These include: the early and late promoters of SV40, the long terminal repeats (LTRs) of Moloney Leukemia Virus and other retroviruses, and the thymidine kinase promoter of Herpes Simplex Virus, among many others. Accordingly, any such constitutive promoters can be used to control transcription of a heterologous gene insert.

Genes that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response, and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic agent in the genetically modified host cell. If the gene encoding the prophylactic or therapeutic agent is under the control of an inducible promoter, delivery of the agent in situ is triggered by exposing the genetically modified cell in situ to conditions for permitting transcription of the prophylactic or therapeutic agent, e.g., by intraperitoneal injection of specific inducers of the inducible promoters which control transcription of the agent. For example, in situ expression by genetically modified host cells of a therapeutic agent encoded by a gene under the control of the metallothionein promoter, is enhanced by contacting the genetically modified cells with a solution containing the appropriate (i.e., inducing) metal ions in situ.

Accordingly, the amount of therapeutic agent that is delivered in situ is regulated by controlling such factors as: (1) the nature of the promoter used to direct transcription of the inserted gene (i.e., whether the promoter is constitutive or inducible, strong or weak); (2) the number of copies of the exogenous gene that are inserted into the host cell; (3) the number of transduced/transfected host cells that are administered (e.g., implanted) to the patient; (4) the size of the implant (e.g., graft or encapsulated expression system); (5) the number of implants; (6) the length of time the transduced/transfected cells or implants are left in place; and (7) the production rate of the prophylactic or therapeutic agent by the genetically modified host cell. Selection and optimization of these factors for delivery of an effective dose of a particular prophylactic or therapeutic agent is deemed to be within the scope of one of skill in the art, taking into account the above-disclosed factors and the clinical profile of the patient.

In addition to at least one promoter and at least one heterologous nucleic acid encoding the prophylactic or therapeutic agent, the expression vector preferably includes a selection gene, for example, a neomycin resistance gene, for facilitating selection of host cells that have been transfected or transduced with the expression vector. Alternatively, the host cells are transfected with two or more expression vectors, at least one vector containing the gene(s) encoding the prophylactic or therapeutic agent(s), the other vector containing a selection gene. The selection of a suitable promoter, enhancer, selection gene and/or signal sequence is deemed to be within the scope of one skilled in the art.

The prophylactic or therapeutic agent can be targeted for delivery to an extracellular, intracellular or membrane location. If it is desirable for the gene product to be secreted from the host cells, the expression vector is designed to include an appropriate secretion signal sequence for secreting the therapeutic gene product from the cell to the extracellular milieu. If it is desirable for the gene product to be within the host cell, this secretion signal sequence is omitted. In a similar manner, the expression vector can be constructed to include retention signal sequences for anchoring the prophylactic or therapeutic agent within the host cell plasma membrane. For example, membrane proteins have hydrophobic transmembrane regions that stop translocation of the protein in the membrane and do not allow the protein to be secreted. The construction of an expression vector including signal sequences for targeting a gene product to a particular location is deemed to be within the scope of one of skill in the art.

In an embodiment, vectors for mammalian host cell gene therapy are viruses, more preferably replication-deficient viruses (described in detail below). Exemplary viral vectors are derived from: Harvey Sarcoma virus; ROUS Sarcoma virus, MPSV, Moloney murine leukemia virus and DNA viruses (e.g., adenovirus) (Temin, H., *Retrovirus vectors for gene transfer*, in GENE TRANSFER, Kucherlapati R, Ed., pp. 149–187, Plenum, (1986)).

Replication-deficient retroviruses are capable of directing synthesis of virion proteins, but are incapable of making infectious particles. Accordingly, these genetically altered retroviral expression vectors have general utility for high-efficiency transduction of genes in cultured cells, and specific utility for use in the method of the present invention. Such retroviruses further have utility for the efficient transduction of genes into host cells in vivo. Retroviruses have been used extensively for transferring genetic material into cells. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with the viral particles) are provided in Kriegler, M. GENE TRANSFER AND EXPRESSION, A LABORATORY MANUAL, W. H. Freeman Co., NY (1990) and Murray, E. J., ed. METHODS IN MOLECULAR BIOLOGY, Vol. 7, Humana Press Inc., Clifton, N.J. (1991).

The major advantage of using retroviruses for gene therapy is that the viruses insert the gene encoding the therapeutic agent into the host cell genome, thereby permitting the exogenous genetic material to be passed on to the progeny of the cell when it divides. In addition, gene promoter sequences in the LTR region have been reported to enhance expression of an inserted coding sequence in a variety of cell types (see e.g., Hilberg et al., *Proc. Natl. Acad. Sci. USA* 84: 5232–5236 (1987); Holland et al., *Proc. Natl. Acad. Sci. USA* 84: 8662–8666 (1987); Valerio et al., *Gene* 84: 419–427 (1989)). In vivo gene therapy using replication-deficient retroviral vectors to deliver a therapeutically effective amount of a therapeutic agent can be efficacious if the efficiency of transduction is high and/or the number of target cells available for transduction is high.

Yet another viral candidate useful as an expression vector for transformation of mammalian host cells is the adenovirus, a double-stranded DNA virus. The adenovirus is frequently responsible for respiratory tract infections in humans and thus appears to have an avidity for the epithelium of the respiratory tract (Straus, S., THE ADENOVIRUS, H. S. Ginsberg, Editor, Plenum Press, NY, p. 451–496 (1984)). Moreover, the adenovirus is infective in a wide range of cell types, including, for example, muscle and epithelial cells (Larrick, J. W. and Burck, K. L., GENE THERAPY. APPLICATION OF MOLECULAR BIOLOGY, Elsevier Science Publishing Co., Inc., NY, p. 71–104 (1991)). The adenovirus also has been used as an expression vector in muscle cells in vivo (Quantin, B., et al., *Proc. Natl. Acad. Sci. USA* 89: 2581–2584 (1992)).

Like the retrovirus, the adenovirus genome is adaptable for use as an expression vector for gene therapy, i.e., by removing the genetic information that controls production of the virus itself (Rosenfeld, M. A., et al., *Science* 252: 431–434 (1991)). Because the adenovirus functions in an extrachromosomal fashion, the recombinant adenovirus does not have the theoretical problem of insertional mutagenesis.

Thus, as will be apparent to one skilled in the art, a variety of suitable viral expression vectors are available for transferring exogenous genetic material into mammalian host cells. The selection of an appropriate expression vector to express an agent for the identification, prevention or treatment of microbial infection amenable to gene replacement therapy and the optimization of the conditions for insertion of the selected expression vector into the cell are within the scope of one of skill in the art without the need for undue experimentation.

In an alternative embodiment, the expression vector is in the form of a plasmid, which is transferred into the target host cells by one of a variety of methods: physical (e.g., microinjection (Capecchi, M. R., *Cell* 22: 479–488 (1980)), electroporation (Andreason, G. L. and Evans, G. A. *Biotechniques* 6: 650–660 (1988)), scrape loading, microparticle bombardment (Johnston, S. A., *Nature* 346: 776–777 (1990)) or by cellular uptake as a chemical complex (e.g., calcium or strontium co-precipitation, complexation with lipid, complexation with ligand) (METHODS IN MOLECULAR BIOLOGY, Vol. 7, GENE TRANSFER AND EXPRESSION PROTOCOLS, Ed. E. J. Murray, Humana Press (1991)). Several commercial products are available for cationic liposome complexation including Lipofectin (Life Technologies, Inc., Gaithersburg, Md.) (Felgner, P. L., et al., *Proc. Natl. Acad. Sci.* 84: 7413–7417 (1987)) and Transfectam™ (ProMega, Madison, Wis.) (Behr, J. P., et al., *Proc. Natl. Acad. Sci. USA* 86: 6982–6986 (1989); Loeffler, J. P., et al., *J. Neurochem.* 54: 1812–1815 (1990)). However, the efficiency of transfection by these methods is highly dependent on the nature of the target cell and accordingly, the conditions for optimal transfection of nucleic acids into host cells using the above-mentioned procedures must be optimized. Such optimization is within the scope of one of skill in the art.

In an embodiment, the preparation of genetically modified host cells contains an amount of cells sufficient to deliver a prophylactically or therapeutically effective dose of a substrate for mammalian transglutaminases of the present invention to the recipient in situ. The determination of an effective dose of the prophylactic or therapeutic agent for a known microbial infection is within the scope of one of skill in the art. Thus, in determining the effective dose, the skilled artisan would consider the condition of the patient, the severity of the condition, as well as the results of clinical studies of the prophylactic or therapeutic agent being administered.

If the genetically modified host cells are not already present in a pharmaceutically acceptable carrier, they are placed in such a carrier prior to administration to the recipient. Such pharmaceutically acceptable carriers include, for example, isotonic saline and other buffers as appropriate to the patient and therapy. The genetically modified cells are administered by, for example, intraperitoneal injecting or implanting the cells or a graft or capsule containing the cells in a host cell-compatible site of the recipient. As used herein, host cell-compatible site refers to a structure, cavity or fluid of the recipient into which the genetically modified cell(s), host cell graft, or encapsulated host cell expression system can be implanted, without triggering adverse physiological consequences. Representative host cell-compatible sites include, for example, the peritoneal, pleural and pericardial cavities. Preferably, the host cell-compatible site communicates with the lymphatic system, thereby enabling delivery of the therapeutic agent to the vascular system.

In one embodiment, the host cell-compatible site may be denuded prior to implanting the cells. Exemplary denuding methods include but are not limited to: (1) injection of distilled water into the site (e.g., the peritoneal cavity) for 20 minutes, followed by scraping off a portion of the epithelial layer; (2) injection of 0.1% buffered trypsin for 20 minutes followed by scraping; (3) removal of epithelial cells by gentle scraping with a cell scraper and (4) touching a piece of Gelfiln (Upjohn, Kalamazoo, Mich.) to the endothelium.

The genetically modified host cells are implanted in a host cell-compatible site, alone or in combination with other genetically modified host cells. Thus, the instant invention embraces a method for modifying the epithelial system of a recipient by using a mixture of genetically modified host cells, such that a first modified cell expresses a first prophylactic or therapeutic agent of the present invention and a second modified cell expresses a second prophylactic or therapeutic agent. Other genetically modified cell types (e.g., hepatocytes, smooth muscle cells, fibroblasts, glial cells, mesothelial cells or keratinocytes) can be added, together with the genetically altered epithelial cells, to produce expression of a complex set of introduced genes. Moreover, more than one recombinant gene can be introduced into each genetically modified cell on the same or different vectors, thereby allowing the expression of multiple prophylactic or therapeutic agents of the present invention by a single cell.

The instant invention further embraces an epithelial cell graft. The graft comprises a plurality of the above-described genetically modified cells attached to a support that is suitable for implantation into a mammalian recipient, preferably into the oral cavity. The support can be formed of a natural or synthetic material. According to another aspect of the invention, an encapsulated host cell expression system is provided. The encapsulated system includes a capsule suitable for implantation into a mammalian recipient and a plurality of the above-described genetically modified host cells contained therein. The capsule can be formed of a synthetic or naturally-occurring material. The formulation of such capsules is known to one of ordinary skill in the art. In contrast to the host cells that are directly implanted into the mammalian recipient (i.e., implanted in a manner such that the genetically modified cells are in direct physical contact with the host cell-compatible site), the encapsulated cells remain isolated (i.e., not in direct physical contact with the site) following implantation. Thus, the encapsulated host cell system is not limited to a capsule including genetically-modified non-immortalized host cells, but may contain genetically modified immortalized host cells.

The invention has been disclosed broadly and illustrated in reference to representative embodiments described above. Those skilled in the art will recognize that various modifications can be made to the present invention without departing from the spirit and scope thereof.

What is claimed is:

1. A method for reducing or inhibiting transglutaminase-mediated adhesion of *Candida albicans* to a mammalian host cell comprising contracting a host cell in vitro with an effective amount of a purified polypeptide comprising the amino acid sequence of SEQ ID NO:1, or an antibody against said purified polypeptide, so that transglutaminase-mediated adhesion of *Candida albicans* to the mammalian host cell is reduced or inhibited.

* * * * *

UNITED STATES PATENT AND TRADEMARK OFFICE
CERTIFICATE OF CORRECTION

| | |
|---|---|
| PATENT NO. | : 7,135,182 B2 |
| APPLICATION NO. | : 10/117121 |
| DATED | : November 14, 2006 |
| INVENTOR(S) | : Sundstrom et al. |

It is certified that error appears in the above-identified patent and that said Letters Patent is hereby corrected as shown below:

At column 2, line 59: please delete "C albicans" and insert --C. albicans--.

At column 2, line 67: please insert --prompts-- between the words "drugs" and "explosion".

At column 3, line 59: please delete "inmmuno-" and insert --immuno- --.

At column 4, line 24: please delete "nuciotide" and insert --nucleotide--.

At column 6, line 43: please delete "MRNA" and insert --mRNA--.

At column 6, line 45: please delete "MRNA" and insert --mRNA--.

At column 6, line 47: please delete "MRNA" and insert --mRNA--.

At column 6, line 55: please delete "Inununoblot" and insert --Immunoblot--.

At column 7, line 40: please delete "$N^{68}$" and insert --$N^{e}$--.

At column 7, line 62: please delete "-" between the words "mediated" and "solely".

At column 8, line 44: please delete "N-terninus" and insert --N-terminus--.

At column 10, line 48: please delete "transglutamninase" and insert --transglutaminase--.

At column 11, line 40: please delete "$Ura^{+}$" and insert --$Ura^{-}$--.

At column 11, line 41: please delete "hwp1/hwp1" and insert --hwp1/HWP1--.

At column 11, line 63: please delete "MRNA" and insert --mRNA--.

At column 12, lines 19-20: please delete "transglutarninase" and insert --transglutaminase--.

At column 15, line 54: please insert --DNA-- between the words "recombinant" and "techniques".

UNITED STATES PATENT AND TRADEMARK OFFICE
CERTIFICATE OF CORRECTION

PATENT NO. : 7,135,182 B2
APPLICATION NO. : 10/117121
DATED : November 14, 2006
INVENTOR(S) : Sundstrom et al.

It is certified that error appears in the above-identified patent and that said Letters Patent is hereby corrected as shown below:

At column 16, line 28: please delete "MRNA" and insert --mRNA--.

At column 19, line 14: please delete "centrif gation" and insert --centrifugation--.

At column 20, line 1: please delete "sulfirric" and insert --sulfuric--.

At column 28, line 51: please insert --retained-- between the words "be" and "within".

At column 31, line 2: please delete "Gelfin" and insert --Gelfilm--.

At column 33, line 23, claim 1: please delete "contracting" and insert --contacting--.

Signed and Sealed this

Twenty-third Day of September, 2008

JON W. DUDAS
*Director of the United States Patent and Trademark Office*